United States Patent
Jung et al.

(10) Patent No.: US 9,549,807 B2
(45) Date of Patent: Jan. 24, 2017

(54) TUBE WITH MODIFIED INNER WALL SURFACE USING PLASMA AND A PREPARATION METHOD THEREOF

(71) Applicant: RESEARCH & BUSINESS FOUNDATION SUNGKYUNKWAN UNIVERSITY, Suwon-si (KR)

(72) Inventors: Dong Geun Jung, Seoul (KR); Yong Ki Cho, Ansan-si (KR); Dae Won Park, Incheon (KR); Heon Yong Park, Yongin-si (KR); Hye Rim Lee, Suwon-si (KR)

(73) Assignee: RESEARCH & BUSINESS FOUNDATION SUNGYUNKWAN UNIVERSITY, Suwon-si (KR)

( * ) Notice: Subject to any disclaimer, the term of this patent is extended or adjusted under 35 U.S.C. 154(b) by 262 days.

(21) Appl. No.: 14/167,251

(22) Filed: Jan. 29, 2014

(65) Prior Publication Data
US 2014/0257450 A1 Sep. 11, 2014

(30) Foreign Application Priority Data
Mar. 7, 2013 (KR) ........................ 10-2013-0024725

(51) Int. Cl.
*A61F 2/06* (2013.01)
*B05D 7/02* (2006.01)
(Continued)

(52) U.S. Cl.
CPC .................. *A61F 2/06* (2013.01); *A61L 27/50* (2013.01); *A61L 27/507* (2013.01); *B05D 1/62* (2013.01);
(Continued)

(58) Field of Classification Search
CPC ....................................................... A61F 2/06
(Continued)

(56) References Cited

U.S. PATENT DOCUMENTS

| 4,656,083 | A | * | 4/1987 | Hoffman | ................... A61F 2/06 128/DIG. 22 |
| 4,718,907 | A | * | 1/1988 | Karwoski | ................ A61F 2/06 204/169 |

(Continued)

FOREIGN PATENT DOCUMENTS

| KR | 10-2009-0006912 A | 1/2009 |
| KR | 10-0970025 | 7/2010 |

(Continued)

OTHER PUBLICATIONS

Lauer et al. "Reduced adhesion of human blood platelets to polyethylene tubing by microplasma surface modification." Journal of Applied Physics. vol. 96 No. 8. Oct. 15, 2004.*

(Continued)

*Primary Examiner* — Cachet Sellman
(74) *Attorney, Agent, or Firm* — NSIP Law

(57) ABSTRACT

The present invention relates to a preparation method of a tube and a transplantable polymer tube prepared by such method, which includes modifying the inner surface of a tube using plasma. A preparation method of a tube may include preparing a tube, modifying the inner surface of the tube using microplasma so as to have reactivity, forming a thin film layer on the modified surface of the tube to prevent aging or impart adhesiveness, and modifying the surface of the thin film layer using microplasma so as to enhance cell adhesion thereon.

16 Claims, 18 Drawing Sheets

(51) Int. Cl.
*B05D 7/22* (2006.01)
*B05D 1/00* (2006.01)
*A61L 27/50* (2006.01)
*A61F 2/00* (2006.01)
*B05D 3/14* (2006.01)

(52) U.S. Cl.
CPC . *B05D 7/02* (2013.01); *B05D 7/22* (2013.01); *A61F 2/0077* (2013.01); *A61F 2240/001* (2013.01); *A61F 2250/0067* (2013.01); *A61L 2400/18* (2013.01); *B05D 3/144* (2013.01)

(58) Field of Classification Search
USPC .............. 427/532, 230, 487, 488, 2.25, 2.28
See application file for complete search history.

(56) References Cited

U.S. PATENT DOCUMENTS

| | | | | |
|---|---|---|---|---|
| 4,846,101 | A * | 7/1989 | Montgomery | A61F 2/062 118/50.1 |
| 4,927,676 | A * | 5/1990 | Williams | A61L 27/507 424/423 |
| 5,370,681 | A * | 12/1994 | Herweck | A61F 2/06 600/36 |
| 6,033,582 | A * | 3/2000 | Lee | A61L 27/3839 204/192.32 |
| 2005/0163816 | A1 * | 7/2005 | Agrawal | A61L 27/3804 424/423 |
| 2006/0034883 | A1 * | 2/2006 | Dang | A61F 2/07 424/422 |
| 2009/0181185 | A1 * | 7/2009 | Grosse | B05D 1/62 427/569 |
| 2010/0298738 | A1 * | 11/2010 | Felts | B05D 1/62 600/576 |

FOREIGN PATENT DOCUMENTS

| | | |
|---|---|---|
| KR | 10-2012-0087049 | 8/2012 |
| KR | 10-1185835 B1 | 9/2012 |

OTHER PUBLICATIONS

Hegemann et al. "Plasma treatment of polymers for surface and adhesion improvement." Nulcear Instruments and Methods in Physics Research Section B: Beam Interactions and Materials and Atoms. vol. 208 pp. 281-286. Aug. 2003.*

Korean Notice of Allowance issued on Jan. 5, 2015 in corresponding Korean Application No. 10-2013-0024725 (2 pages, in Korean).

Korean Office Action issued on Jun. 19, 2014 in Korean Intellectual Patent Office for the corresponding Korean Application No. 10-2013-0024725 (6 pages in Korean).

* cited by examiner (a)

(b)

TUBE WITH MODIFIED INNER WALL SURFACE USING PLASMA AND A PREPARATION METHOD THEREOF

CROSS-REFERENCE TO RELATED APPLICATIONS

This application claims the benefit under 35 USC 119(a) of Korean Patent Application No. 10-2013-0024725 filed on Mar. 7, 2013, in the Korean Intellectual Property Office, the entire disclosure of which is incorporated herein by reference for all purposes.

BACKGROUND OF THE INVENTION

1. Field of the Invention

The present invention relates to a preparation method of a tube, which includes modifying the inner surface of a tube using plasma; a preparation method of a tube, which includes preparing a tube, modifying the inner surface of the tube using microplasma so as to have reactivity, forming a thin film layer on the modified surface of the tube to prevent aging or impart adhesiveness, and modifying the surface of the thin film layer using microplasma so as to enhance cell adhesion thereon; and a transplantable polymer tube prepared by the above method.

2. Description of the Related Art

Vascular diseases are caused by a hardening of the arteries due to a thickening of the inside of the arteries mainly as a result of fat accumulation or plaque (or atheroma). The arteries are blood vessels that supply blood, oxygen and nutrients to the whole body from the heart. Thus, the narrowed and hardened arteries disturb the flow of blood and make it difficult to efficiently supply the above materials to individual organs. Such an insufficient supply of blood incurs dysfunction, tissue damage, etc., and in severe cases, leads to death. Hence, in order to treat vascular diseases, drugs which relax blood vessels are administered, but drug treatment merely mitigates symptoms and does not cure vascular diseases, and may thus result in lifelong drug dependence, which is undesirable. Other treatment methods may include surgical methods in which a damaged blood vessel is removed and an artificial blood vessel is transplanted into the corresponding portion.

Although methods of transplanting arteries or veins of donors have been initially implemented, they suffer from low success rates due to rejection or sclerosis. Hence, research and development into synthetic (artificial) blood vessels has been conducted. Artificial blood vessels for transplantation have to be made of materials which are harmless to the human body and have high biocompatibility. Furthermore, these materials should not be rejected by the immune system and should be able to be maintained for a long time in vivo. Also, there should be no cases in which blood vessels are clogged by precipitation of proteins or lipids or due to thrombosis.

Typically, polymer materials, which are very stable in vivo, are being utilized as biomaterials in terms of artificial blood vessels, artificial hearts, alternatives to metal stents, etc. Among these, polymer tubes are variously applied for use as hemodialysis tubes, human circulatory system transplantation tubes, tubes for diagnostic bio-kits, syringes, etc. The polymer tubes are surface-modified depending on end use, and such surface modification is mainly performed only on the outer surface. Examples of the methods for surface treatment include electron beam treatment, ion beam treatment, coating methods, wet methods, etc. using vacuum techniques and plasma. This surface modification enables the polymer material to be changed to have a reactive coupling structure of the surface which is different from a reactive coupling structure of the bulk polymer material which is the unmodified portion.

Surface modification techniques for a biologically reactive outer surface include surface modification of human circulatory system transplantation tubes using a wet method as disclosed in Korean Patent Nos. 10-1034654, 10-1119011 and 10-1161151, and modification of a fluorinated polymer into a superhydrophobic surface using vacuum plasma as disclosed in Korean Patent No. 10-1185835.

Meanwhile, as biomaterials to be transplanted in vivo, the inner surface of polymers preferably has to have thrombotic resistance and/or inflammation inhibitory ability in order to prevent clogging due to thrombosis and inflammation. Also, the outer surface thereof should have high compatibility with the peripheral cells, and should be able to inhibit protein reactions and inflammation. In the case where typical fluorinated polymers, which are hydrophobic and inert without reactivity to materials having different characteristics, are provided in the form of a tube, both the inner and outer surfaces thereof are inert and hydrophobic. Thus, the inert and hydrophobic polymers may be imparted with hydrophilicity using the above surface modification techniques or may be deposited with biomaterials having increased reactivity, so that such polymers may be modified into materials suitable for human transplantation.

To typically impart superhydrophobicity onto the surface of a material, the corresponding processes have been developed using conventional surface treatment methods for drugs. However, such surface modification methods mostly include modification of the outer surface of tubes, and techniques for modifying the inner surface thereof are very limited.

SUMMARY OF THE INVENTION

Culminating in the present invention, intensive and thorough research into modification methods for improving the reactivity and hydrophilicity of the surface of various polymer materials including fluorinated polymers were carried out by the present inventors in an attempt to solve the problems encountered in the related art, which led to the discovery of surface modification conditions able to increase reactivity by depositing a coating material using microplasma techniques, allowing for a surface modification technique for the inner surface of polymers.

Accordingly, an object of the present invention is to provide a preparation method of a tube, which includes modifying the inner surface of a tube using plasma.

Another object of the present invention is to provide a preparation method of a tube, which includes preparing a tube, modifying the inner surface of the tube using microplasma so as to have reactivity, forming a thin film layer on the modified surface of the tube to prevent aging or impart adhesiveness, and modifying the surface of the thin film layer using microplasma so as to enhance cell adhesion thereon.

A further object of the present invention is to provide a transplantable polymer tube, prepared by the above method.

In order to accomplish the above objects, an aspect of the present invention provides a preparation method of a tube, which includes modifying the inner surface of a tube using plasma.

Another aspect of the present invention provides a preparation method of a tube, including 1) preparing a tube; 2)

modifying the inner surface of the tube using microplasma so as to have reactivity; 3) forming a thin film layer on the modified surface of the tube to prevent aging or impart adhesiveness; and 4) modifying the surface of the thin film layer using microplasma so as to enhance cell adhesion.

A further aspect of the present invention provides a transplantable polymer tube, prepared by the above method.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF SPECIFIC EMBODIMENTS

Figure 1:
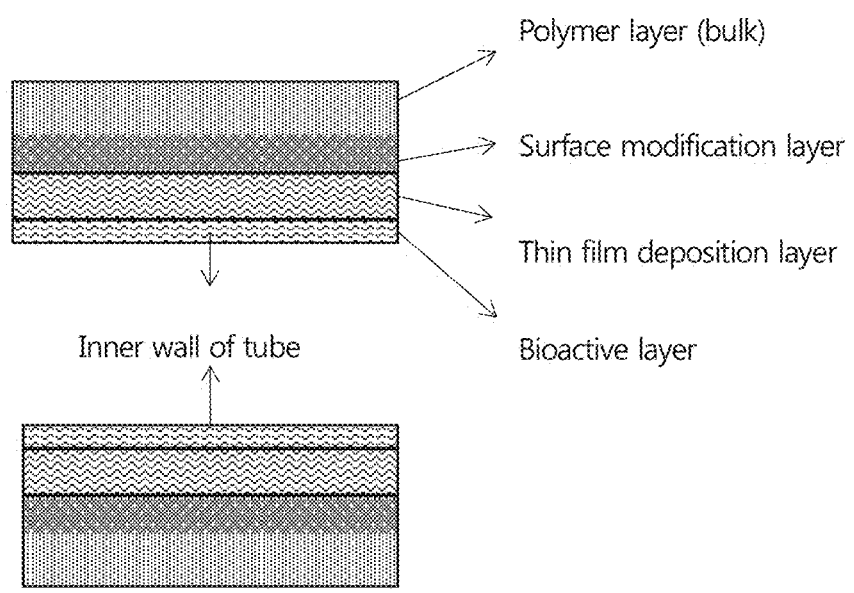
FIG. 1 schematically illustrates layers having various properties formed on the inner surface of a tube by the reaction of individual steps using microplasma in a preparation method according to the present invention.
Figure 2:
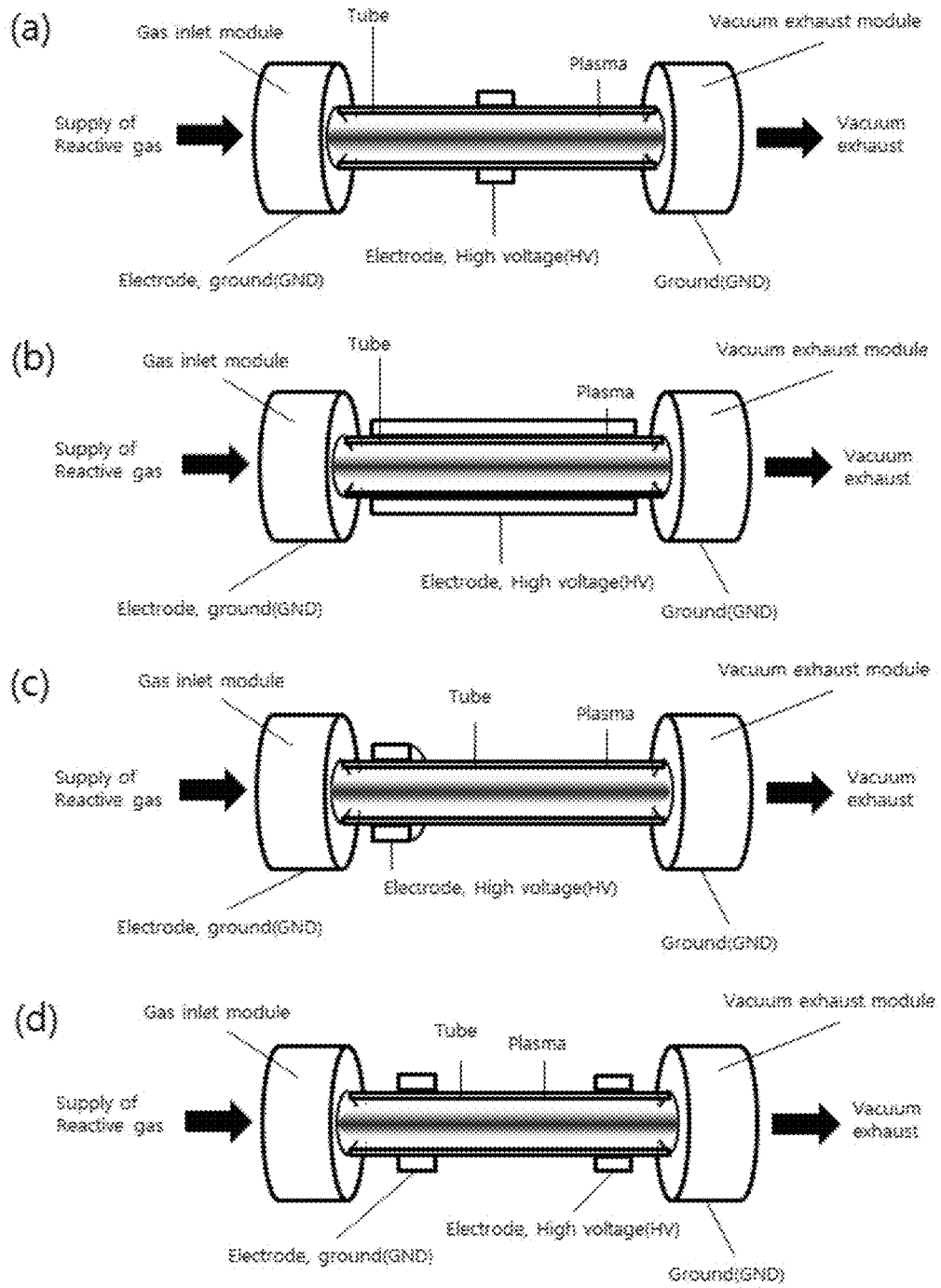
FIGS. 2(a) to 2(d) schematically illustrate various devices for forming microplasma in a tube under a vacuum condition.
Figure 3:
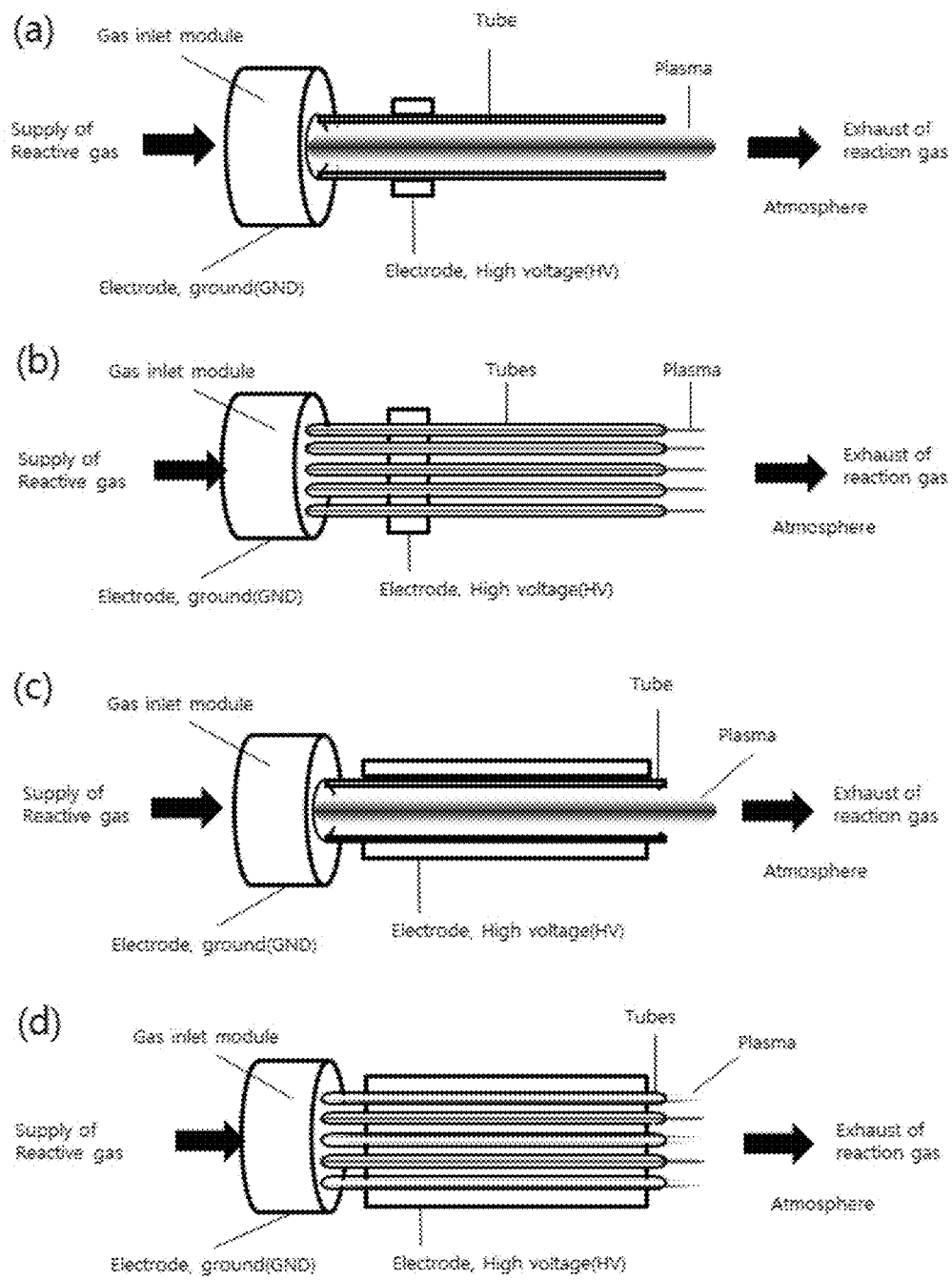
FIGS. 3(a) to 3(d) schematically illustrate various devices for forming microplasma in a tube under an atmospheric condition.

According to a first embodiment of the present invention, there is provided a preparation method of a tube, which includes modifying the inner surface of the tube using plasma.

As such, the modification using plasma may comprise adjusting the extent of hydrophilicity and hydrophobicity of the inner surface of the tube by variously changing the corresponding reaction conditions. The reaction conditions which affect the reaction may include the kind of reaction gas, ratio thereof, or plasma treatment time.

Preferably, the preparation method of the tube according to the present invention includes modifying the inner surface of the tube using microplasma so as to enhance cell adhesion thereon.

Non-limited examples of the tube in the present invention may include superhydrophobic fluorinated hydrocarbon polymer tubes made of polytetrafluoroethylene (PTFE), a fluorinated ethylene propylene copolymer (FEP), an ethylene tetrafluoroethylene copolymer, ethylene chlorotrifluoroethylene (ETFE), perfluoroalkoxy (PFA) or polyvinyliden fluoride (PVDF); biocompatible polymer tubes made of polyethylene terephthalate (PET), poly(2-hydroxyethyl methacrylate) (PHEMA), polyvinylpyrrolidone (PVP), polyethylene (PE), polyethylene glycol (PEG a.k.a. polyethylene oxide; PEO or polyoxyethylene; POE), polyvinyl alcohol (PVOH, PVA or PVA1), polypropylene (PP) or polyurethane (PU); and metal tubes made of nitinol (NiTi), titanium, stainless steel 316L (SUS 316L) or a cobalt-chromium alloy.

As used herein, the term "fluorinated hydrocarbon polymer" refers to a polymer composed exclusively of fluorine, carbon and hydrogen atoms wherein the backbone thereof includes carbon-carbon bonds and the other bonds including hydrogen atoms, fluorine atoms, alkyl, partially fluorinated alkyl or perfluoroalkyl. This polymer typically has high molecular weight and high density but low intermolecular force. Because this polymer includes a backbone of strong carbon-carbon bonds, it has high strength, and low reactivity due to strong carbon-fluorine or carbon-hydrogen bonds therein, making it difficult to perform modification. In a uniformly fluorinated polymer, there exists a weak fleeting dipole formed by London dispersion force resulting from lowered atomic polarizability due to high electrical negativity of fluorine atoms, thereby exhibiting low intermolecular attraction and non-polarity and/or hydrophobicity.

Accordingly, in order to modify the inner surface of the biocompatible tube to be transplantable, modifying the inner surface of the tube using microplasma so as to enhance the cell adhesion thereon is preferably performed.

Preferably, the reaction gas is a gas mixture of hydrogen and argon, but the present invention is not limited thereto. Furthermore, in order for efficient modification, the gas mixture may include argon and hydrogen mixed at a volume ratio of 1:3~1:7.

Modifying the inner surface of the tube in the present invention as above may be widely applied not only to polymers utilized as biomaterials but also to various materials such as metals, plastics, etc., and the materials thus modified may be utilized in a variety of fields. Herein, the plastics have a low dielectric constant similar to the biocompatible polymers, and thus may be optimized by selectively using a reaction gas so as to be adapted for end use via a polymer surface modification method using microplasma.

Also, metals alone have durability and strength and may thus be variously utilized, but are disadvantageous because they may become oxidized and thus may corrode when exposed to air and/or moisture. Because such metals are electrically conductive, the inside of the tube-shaped metal may be subjected to surface treatment using various plasma generation sources such as typical DC (including DC pulse), RF, MF, etc., in addition to microplasma. Surface treatment of metal may include reactive surface treatment, and surface modification of bio parts for bio-applications by forming a functional thin film, and as well, may be variously industrially applied and thus may be utilized to improve functions of car parts, mechanical parts and electronic parts. Typical examples of inductively synthesized films may include a protective film for preventing corrosion of metal by depositing, on the inner surface of a tube, a hydrocarbon thin film which is more noble in corrosion behavior compared to metal, a film having high chemical resistance by depositing an inert material, a film for preventing aggregation of a reactive material by depositing a highly lubricating material, a film having high wear resistance by depositing a material having high hardness, etc.

As used herein, the term "microplasma" refers to plasma of a small dimension ranging from tens to thousands of micrometers. Plasma indicates a fourth state of a material, other than solid, liquid and gas, and when gas is heated, molecules or atoms donate or accept electrons and are thus ionized, thereby forming plasma containing electrically charged particles. Microplasma may be produced under various temperature and pressure conditions, and exists as thermal or non-thermal plasma. Microplasma may be present in the wide pressure range from tens of mTorr to atmospheric pressure, and thus non-thermal microplasma that may maintain its state at standard temperature and pressure is readily available and highly accessible as it may be easily sustained and manipulated under standard conditions. Meanwhile, the formation of plasma in a small dimension is possible at high pressure. Accordingly, plasma may be used for commercial, industrial and medical applications.

Specifically, when energy is applied to gas, the internal electrons of gas molecules or atoms are excited and move up to higher energy levels. If the energy applied is high enough, outermost electrons may even be stripped off the molecules or atoms, thus forming ions. Electrons, molecules (or atoms), excited species and ions form a soup of species which involves many interactions between species and demonstrate collective behavior under the influence of external electric or magnetic fields. Light always accompanies plasma: as the excited species relax and move to lower energy levels, releasing the energy in the form of light.

The microplasma may be produced by direct current (DC) discharge, hollow cathode discharge (HCD), dielectric barrier discharge (DBD), corona discharge or microwave discharge. Furthermore, it may be inductively coupled plasma (ICP) or capacitively coupled plasma (CCP) formed by radio frequencies corresponding to ultra-high frequencies. Preferably, microplasma is formed by dielectric barrier discharge which is electrical discharge between two electrodes spaced apart by a dielectric barrier, but the present invention is not limited thereto.

In the preparation method of the tube according to the present invention, in order to prevent the inner surface of the tube or the microplasma-treated surface from aging, a plasma-polymerized thin film layer may be formed by accumulating a hydrocarbon precursor on the inner surface of the tube using plasma. Also, this thin film layer may enhance adhesiveness of a surface modification layer which may be additionally introduced.

Preferably, the thin film layer is a hydrocarbon film layer, but the present invention is not limited thereto.

The hydrocarbon film layer may be formed by plasma polymerization using a gas mixture of acetylene and argon. As such, it is possible to form the thin film layer having a desired thickness by adjusting the reaction time. Preferably, the thickness of the hydrocarbon film layer is 50-250 nm.

Figure 5:
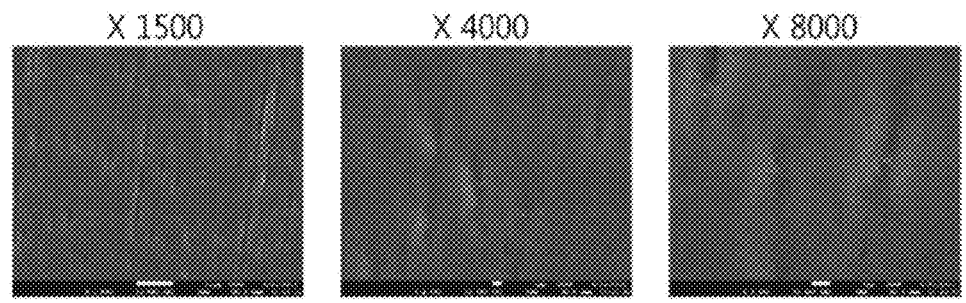
FIG. 5 illustrates SEM images of a hydrocarbon thin film deposited for 10 min.
Figure 7:
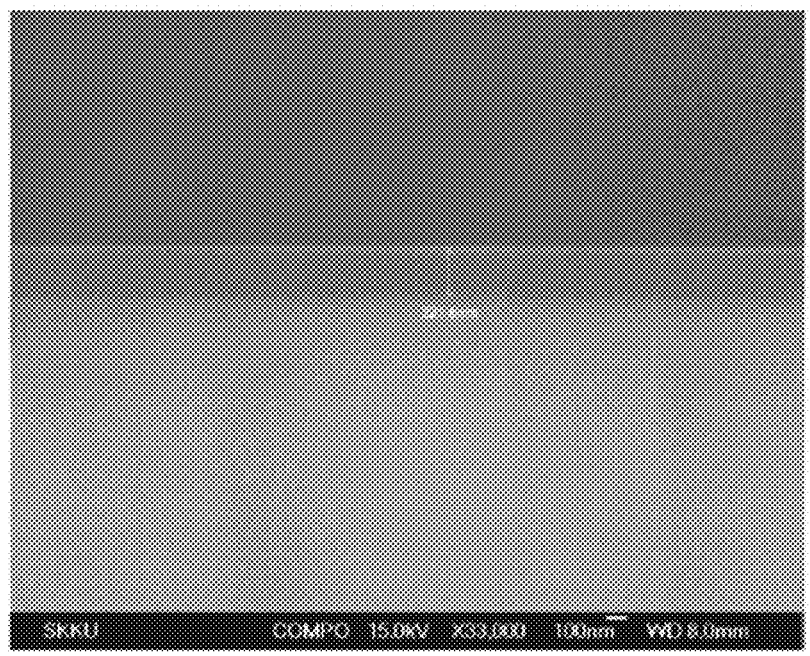
FIG. 7 illustrates a SEM image of a hydrocarbon thin film deposited for 10 minutes on a silicon wafer to measure thickness.

In specific exemplary embodiments, plasma polymerization was induced using a gas mixture of acetylene and argon, and a coating process for 10 minutes resulted in the modified surface which was made uniform and very smooth while preventing aging thereof (FIG. 5). Through testing on a silicon wafer, the thickness of the applied thin film layer was determined to be about 220 nm (FIG. 7).

Preferably, the preparation method for a transplantable tube according to the present invention may further include modifying the inner surface of the microplasma-treated tube or the surface of the thin film layer using microplasma so as to enhance cell adhesion.

Preferably, this additional modification step is carried out using a gas mixture of oxygen and argon or a gas mixture of nitrogen and argon as the reaction gas.

In the case where oxygen is used as the reaction gas in the above modification step, when the reaction time is lengthened, etching begins to take place. Hence, the reaction is preferably carried out within a comparatively short time. In the case where nitrogen is used, nitrogen has lower surface modification efficiency compared to oxygen, and thus the reaction time may be comparatively lengthened to obtain desired effects. Preferably the reaction is carried out for 20~80 seconds when using oxygen as the reaction gas, or for 4~8 minutes when using nitrogen as the reaction gas.

As mentioned above, microplasma may be formed in the wide pressure range from tens of mTorr to atmospheric pressure. Thus, the microplasma is preferably formed by atmospheric pressure discharge, but the present invention is not limited thereto. In the case where microplasma is produced by atmospheric pressure discharge, a vacuum treatment procedure using a pump may be excluded, and thus the production device may be simplified and the production process may become simpler. Also, while the gas temperature is maintained at a low value, chemically activated excited species and reactive species may be easily produced, and there is no need for a vacuum environment, thereby making it easy to treat products having various shapes and to enlarge the plasma treatment area.

In the tube according to the present invention, the inner surface thereof may be subjected to 1) modification via treatment of a reaction gas or 2) formation of a thin film layer using polymerization, and these steps may be repeated regardless of the sequence thereof.

Preferably, the inner wall of the polymer tube may be enhanced in cell adhesion. Typically, in the case of cells which are cultured by being attaching to a solid, cells exhibit very low adhesion to the hydrophobic surface but improved adhesion to the hydrophilic surface. This is applied to general cell culture dishes, in which the culture of cells which are mostly subjected to adherent culture is performed using a culture dish having a hydrophilic surface, whereas the culture of cells to undergo suspension culture or to suppress adherent culture is performed using a culture dish having a hydrophobic surface or a culture dish treated with a material which suppresses attachment of cells. In the polymer tube prepared according to the present invention, the inner surface of the tube becomes hydrophilic via the series of procedures as above, thus facilitating attachment of the cells to the surface of the tube. Therefore, the polymer tube according to the present invention may be enhanced in terms of cell adhesion on the inner wall thereof.

Figure 21:
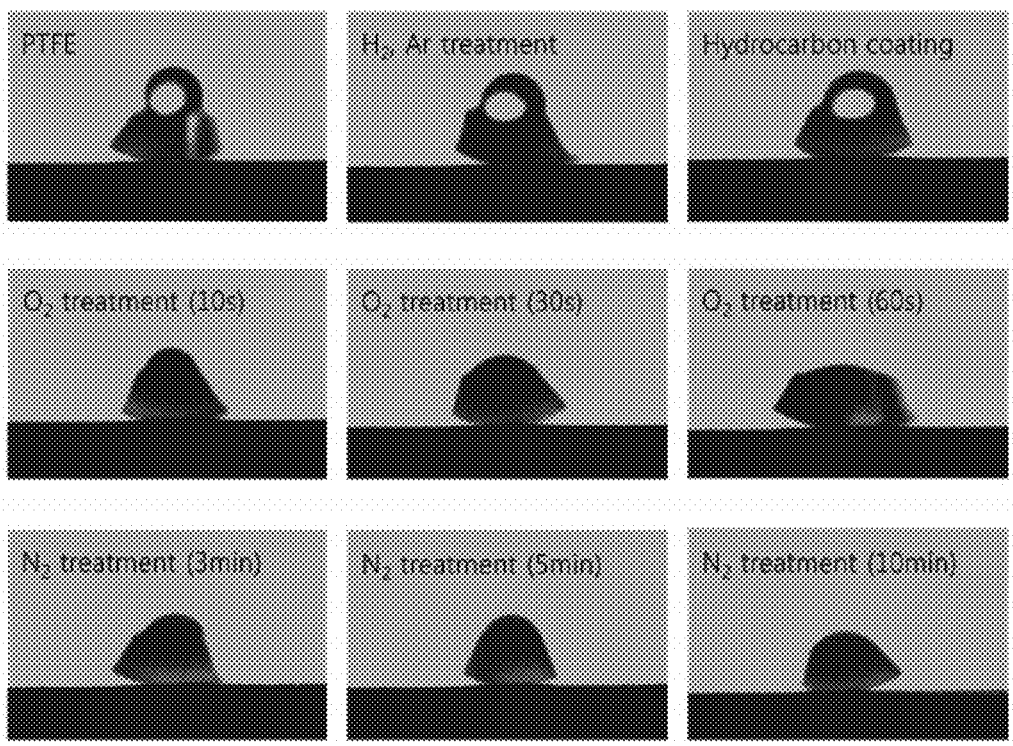
FIG. 21 illustrates water contact images under a series of preparation conditions.
Figure 23:
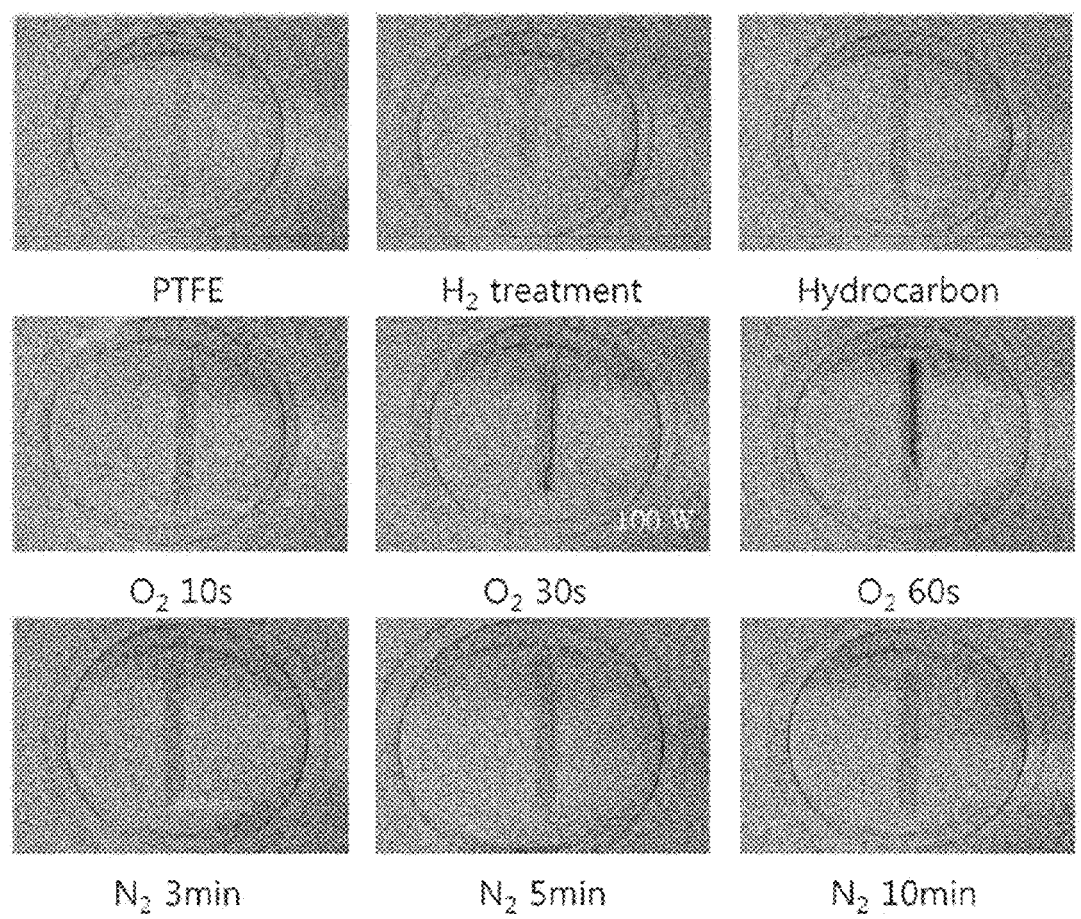
FIG. 23 illustrates the extent of culture of smooth muscle cells depending on preparation conditions via cytoplasmic staining.
Figure 24:
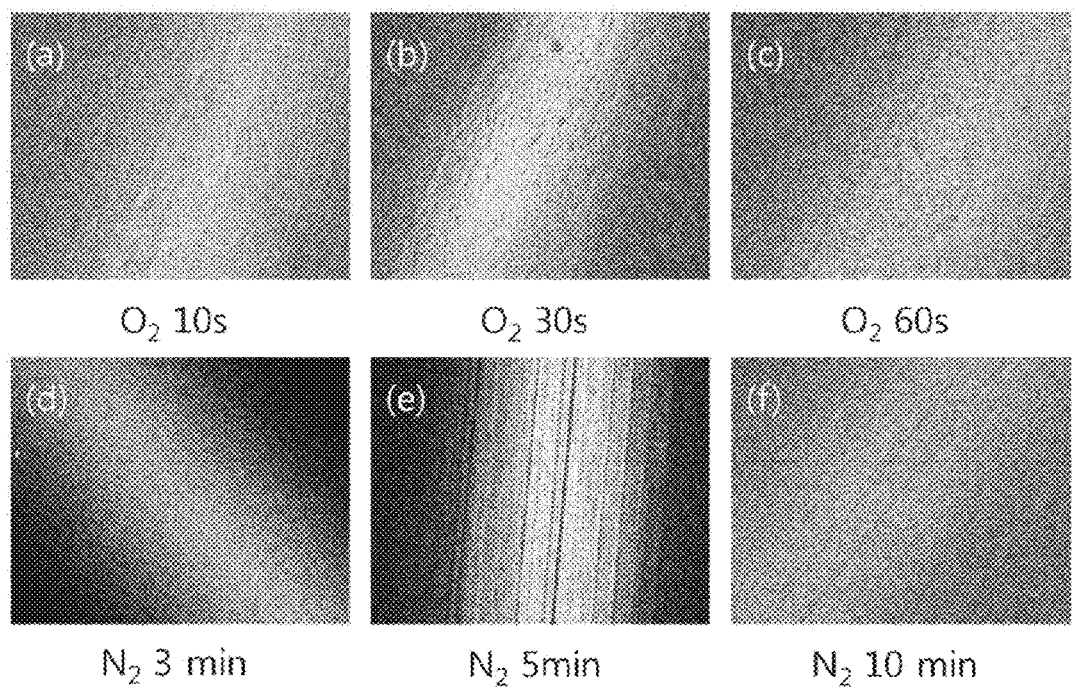
FIGS. 24(a), 24(b) and 24(c) illustrate optical microscope images of the morphology of smooth muscle cells cultured on the inner wall of the surface-modified PTFE tube at different surface modification times of 10, 30 and 60 sec, respectively, using oxygen.
FIGS. 24(d), 24(e) and 24(f) illustrate optical microscope images of the morphology of smooth muscle cells cultured on the inner wall of the surface-modified PTFE tube at different surface modification times of 3, 5 and 10 min, respectively, using nitrogen

In specific exemplary embodiments, non-treated PTFE shows very high hydrophobicity and thus a water drop applied on the surface of PTFE can be seen to be almost spherical. Surface modification using a gas mixture of argon and hydrogen and/or introduction of a hydrocarbon thin film layer following the surface modification increased hydrophilicty and thus the contact angle of water drop was slightly decreased (FIG. 21). Also, upon treatment with microplasma for a period of time of tens of seconds or ones of minutes using a reaction gas containing oxygen or nitrogen after the surface modification and the formation of the thin film layer, hydrophilicty was remarkably increased (FIG. 21), and thus cells could be attached to the tube treated with microplasma using oxygen or nitrogen after sequentially implementing the surface modification and introduction of the thin film layer (FIGS. 23 and 24).

A second embodiment of the present invention provides a preparation method for a tube, including 1) preparing a tube; 2) modifying the inner surface of the tube using microplasma so as to have reactivity; 3) forming a thin film layer on the modified surface of the tube to prevent aging or impart adhesiveness; and 4) modifying the surface of the thin film layer using microplasma so as to enhance cell adhesion.

As used herein, the term "hydrophobic" refers to a surface property, wherein, when liquid comes into contact with the surface of solid, wettability is very low and thus a water drop present on the surface is formed to be round, and wettability and/or hydrophobicity are determined by contact angle ($\theta$). The contact angle is defined as an angle formed between the surface and the liquid drop, and the greater the hydrophobicity, the higher the contact angle. For example, when the contact angle is 0°, hydrophilicity is very high, resulting in a completely wet state. When the contact angle is 180°, hydrophobicity is very high and thus a completely non-wet state may result. The case where the contact angle is less than 90° refers to hydrophilicity, and the case where the contact angle is greater than 90° refers to hydrophobicity, and especially, the case where the contact angle is 160° or more indicates superhydrophobicity. Therefore, the polymer tube according to the present invention is hydrophobic and thus has a contact angle much greater than 90°, and thereby a water drop on the surface of the tube is maintained to be almost round (FIG. 21).

The hydrophobic fluorinated hydrocarbon polymer contains a plurality of carbon-fluorine bonds as mentioned above and thus is hydrophobic, and makes it difficult to modify because of the carbon-fluorine bonds having low reactivity. In Step 2), modification to obtain a reactive surface is substitution of the fluorine-carbon bond of the fluorinated hydrocarbon polymer with a hydrogen-carbon bond, so that the hydrophobic and inert surface is converted into a hydrophilic and reactive surface. As such, this modification may be conducted using microplasma in the presence of a reaction gas.

Non-limited examples of the hydrophobic fluorinated hydrocarbon polymer are mentioned above. Preferably useful is polytetrafluoroethylene.

As used herein, the term "polytetrafluoroethylene" is abbreviated to PTFE, which is a synthetic fluorinated polymer under the brand name of Teflon commercially available from DuPont. PTFE is a compound composed exclusively of carbon and fluorine with high molecular weight, and is hydrophobic and thus is not wet by water or a material containing water, and exhibits low London dispersion force due to high electrical negativity of fluorine. Also, PTFE is a kind of solid having a low coefficient of friction and thus may be variously utilized as a non-adherent coating material. Also, PTFE has very low reactivity due to strong carbon-fluorine bonds and is thus used for vessels or tubes in contact with reactive and/or corrosive materials. Furthermore, PTFE is useful as a lubricant because of low frictional force thereof.

Figure 10:
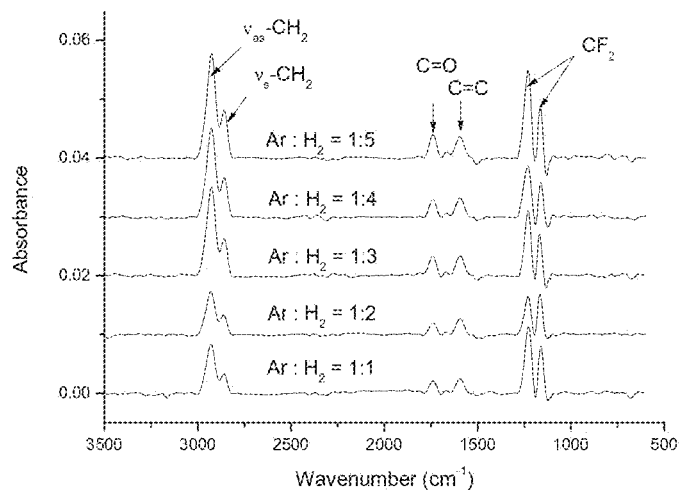
FIG. 10 illustrates FTIR-ATR spectra of the hydrogen plasma treated surface depending on changes in the proportion of hydrogen gas in the reaction gas.
Figure 11:
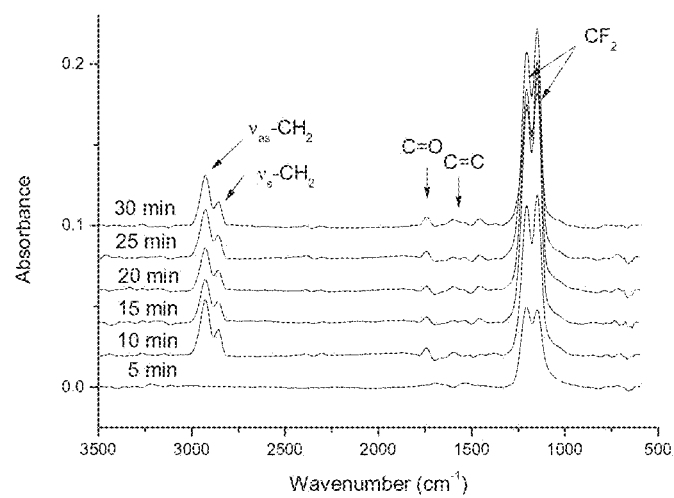
FIG. 11 illustrates FTIR-ATR spectra depending on the hydrogen plasma treatment time.

In specific exemplary embodiments, microplasma was generated in the tube by means of various discharge methods as illustrated in FIGS. 2(a) to 2(d) and 3(a) to 3(d) using a gas mixture comprising inert gas, argon and hydrogen, as the reaction gas, thus producing hydrogen in the form of active species, so that the activated hydrogen having high energy could replace the exposed carbon-fluorine bond with the carbon-hydrogen bond on the inner surface of the highly fluorinated tube having low reactivity, thereby imparting hydrophilicity and ensuring reactivity (FIGS. 10, 11 and 21).

However, the surface modified by such microplasma treatment has a property in which it returns to its original polymer state over time so long as additional treatment is not further performed. This is called aging. In order to prevent such aging, a hydrocarbon precursor may be accumulated on the inner surface of the tube using plasma, thus forming a plasma-polymerized thin film layer. Also, this thin film layer may enhance adhesiveness of a bioactive layer which will be additionally introduced.

Preferably, modifying the surface of the thin film layer using the microplasma so as to enhance cell adhesion is further performed.

A third embodiment of the present invention provides a transplantable polymer tube, prepared by the above method.

The polymer tube is made of a biocompatible polymer and may thus be directly transplanted in vivo. Also, the tube with the hydrophobic inner surface of which is modified to be hydrophilic using the above method is enhanced in adhesion of vascular smooth muscle cells. Therefore, as the polymer tube has a smooth surface so as to enhance adhesion of vascular smooth muscle cells and suppress attachment of proteins or platelets, it may be manufactured into artificial blood vessels, etc. and may thus be transplanted in vivo.

A better understanding of the present invention may be obtained via the following examples which are set forth to illustrate, but are not to be construed as limiting the present invention.

Example 1

Modification of Inner Surface of Tube Using Microplasma

Used as the tube in which the inner surface was to be modified was a biocompatible PTFE tube having an inner diameter of 4 mm, an outer diameter of 6 mm and a thickness of 1 mm. Before surface modification, the tube was cut to a size of 30 cm and impurities were removed from the cut surface using a nitrogen ($N_2$) gun. The PTFE tube was were installed between the gas inlet module and the vacuum evacuation module of a microplasma system, and the inside of the tube was then made vacuous using a rotary type vacuum pump. Meanwhile, a copper electrode having a width of 1.5 cm to enclose the outer surface of the PTFE tube was prepared and fixed at a position distant by 10 cm from the gas inlet module. The copper electrode was connected with an alternating current (AC) source, and a ground electrode was connected to a position at which the tube and the gas inlet module were connected.

Microplasma was used to modify the inner surface of the PTFE tube, and a reaction gas was composed of hydrogen ($H_2$, 99.99%) and argon (Ar, 99.99%). Using a mass flow controller (MFC), hydrogen gas and argon gas were respectively fed at 50 sccm and 10 sccm into the mixing chamber, and the gas mixture was allowed to flow into the PTFE tube. Useful as a plasma generator was an AC source having a frequency of 40 kHz and a maximum voltage of 2 kV, and the inner surface of the PTFE tube was subjected to plasma treatment at 70 W for 10 min. Upon plasma treatment, the inner pressure of the tube was maintained at 430 mTorr. At this time, the frequency was 40 kHz, and the voltage was 1.2 kV. By the plasma treatment above, fluorine on the inner surface of the PTFE tube was partially substituted with hydrogen.

Example 2

Introduction of Thin Film Layer Using Plasma Polymerization

In order to form a nano organic thin film after surface treatment, acetylene gas ($C_2H_2$, 99.99%) was used, and argon gas of 20 sccm was fed into the mixing chamber to induce efficient discharge. The vacuum state of the tube was maintained using a rotary pump, and the inner pressure of the tube containing acetylene gas and argon gas was kept at 220 mTorr. The discharge power of microplasma used for forming the nano organic thin film was 80 W, the frequency and voltage were 40 kHz and 1.3 kV, respectively, and the thin film deposition time was 10 min. The deposition process performed in the microplasma resulted in forming an amorphous hydrocarbon thin film via a plasma polymerization reaction by a radical.

Example 3

Enhancement of Cell Adhesion and Hydrophilization Using Microplasma

The surface deposited nano organic thin film, that is, the amorphous hydrocarbon thin film was modified using a reaction gas so as to have bioactivity. To this end, oxygen ($O_2$, 99.99%) gas and nitrogen ($N_2$, 99.99%) gas were separately used. In the case of surface modification using oxygen, oxygen and argon were fed at 20 sccm each into the mixing chamber using MFC. At this time, the inner pressure of the tube was maintained at 250 mTorr. In the case of surface modification using nitrogen, nitrogen and argon were fed at 20 sccm each into the mixing chamber using MFC, and the inner pressure of the tube was maintained at 260 mTorr. Surface modification using oxygen or nitrogen was carried out under conditions of a plasma power of 80 W, a frequency of 40 kHz, and a voltage of 1.3 kV. Upon oxygen treatment, because a long reaction time causes etching of the thin film, the reaction was carried out for 10, 30 and 60 seconds corresponding to comparatively short times. Because nitrogen has less severe thin film etching problems, the reaction was conducted for 3, 5 and 10 min. The cross-section of the tube resulting from the procedures of Examples 1 to 3 is schematically illustrated in FIG. 1.

Test Example 1

Culture and Attachment of Smooth Muscle Cells

Rat vascular smooth muscle cells were cultured in a culture medium containing high glucose Dulbecco's modified eagle's medium (DMEM, Wel GENE INC.) including 4500 mg/l of glucose supplemented with 10% fetal bovine serum (FBS) in which the concentration of FBS was adjusted to 20%. This culture medium was added with 1% penicillin/streptomycin (Wel GENE Inc.) in order to prevent contamination and deterioration. The cells were cultured in a cell incubator at 37° C. and 5% $CO_2$. The cells cultured in a state of being attached to the bottom of a culture dish were washed with 1×PBS (phosphate buffered saline; 8% NaCl, 0.2 g KCl, 1.14 g $Na_2HPO_4$, 0.2 g $KH_2PO_4$/L) at intervals of two or three days, and then treated with 1× trypsin/EDTA (Wel GENE Inc.) in an amount of 2 ml, so that the cells were stripped off the culture dish. The separation of the cells was observed using a microscope, and the reaction was stopped by adding 10 ml of a culture medium to the 100 mm culture dish, and the resulting mixture was recovered, placed in a centrifuge and rotated at 3000 rpm for 3 min, whereby only the cells were recovered. The recovered cells were aliquoted again at an appropriate cell concentration in a new culture dish so that the culture continued, or the subsequent testing was conducted using the recovered cells.

To evaluate the adhesion of vascular smooth muscle cells on the surface-modified PTFE tube according to the present invention, the PTFE tube, resulting from modification to be hydrophilic, deposition with the hydrocarbon thin film and then surface modification with oxygen or nitrogen through the procedures described in Examples 1 to 3, was cut in half and both ends thereof were closed, and smooth muscle cells were uniformly aliquoted in the tube using a pipette. After 24 hr, the culture medium was removed, the cells which were not attached to the surface of the tube were removed via washing with 1×PBS, and cytoplasms were stained with eosin B and thus changes in color of the inner surface of the tube were observed. Also, in samples without cytoplasmic staining, the cells adsorbed to the inner wall of PTFE were directly observed using an optical microscope.

Test Example 2

Field Emission Scanning Electron Microscope (FE-SEM)

To observe changes in morphology of the inner surface of the tube in individual processes and to measure thickness of the deposited organic thin film, FE-SEM was used. Accordingly, changes in morphology of the inner surface of the tube depending on the process steps were observed, and a silicon wafer was inserted into the tube and the thickness of a hydrocarbon thin film formed thereon was measured, thereby determining the thickness of the thin film formed on the inner surface of the PTFE tube. The device used was JSM-7001F, accelerating voltage was 0.2-30 kV, resolution was 3 nm at 1 kV and was 1.2 nm at 30 kV, and magnification was in the range of ten to million times.

Figure 4:
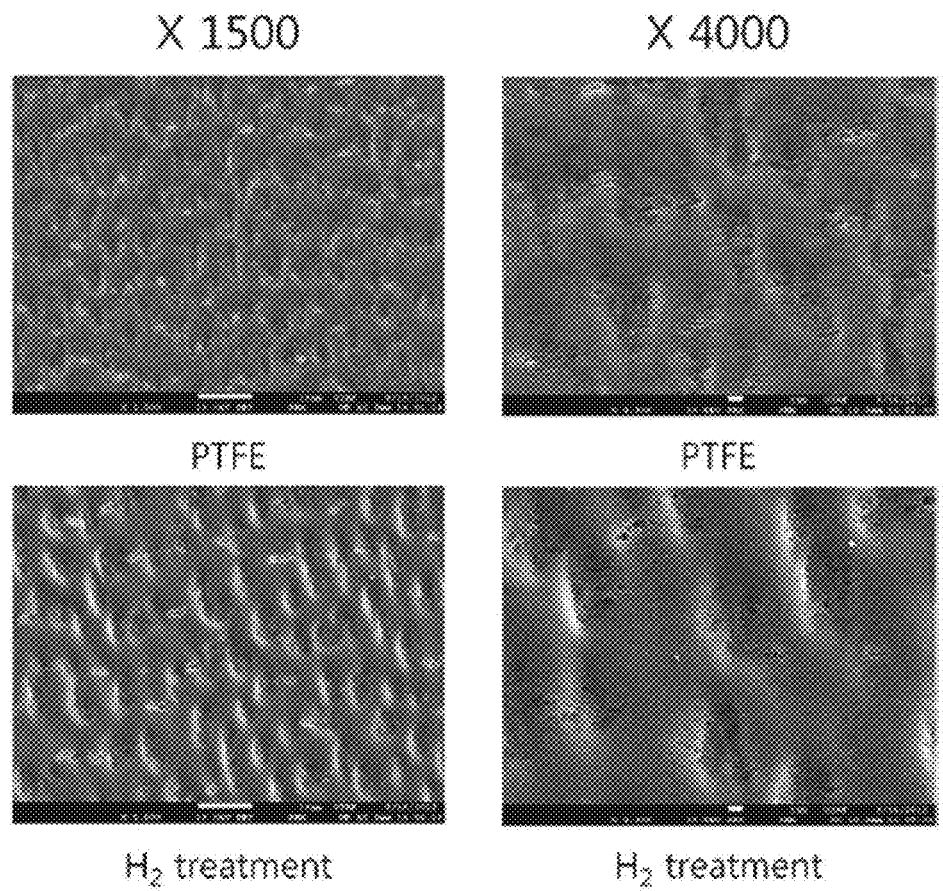
FIG. 4 illustrates scanning electron microscope (SEM) images of the inner wall of a PTFE tube before and after hydrogen plasma treatment.

FIG. 4 illustrates SEM images of the inner wall of a PTFE tube before and after hydrogen plasma treatment. After hydrogen plasma treatment on PTFE, the surface of the PTFE tube was confirmed to be flattened while maintaining the inner structure thereof.

Figure 6:
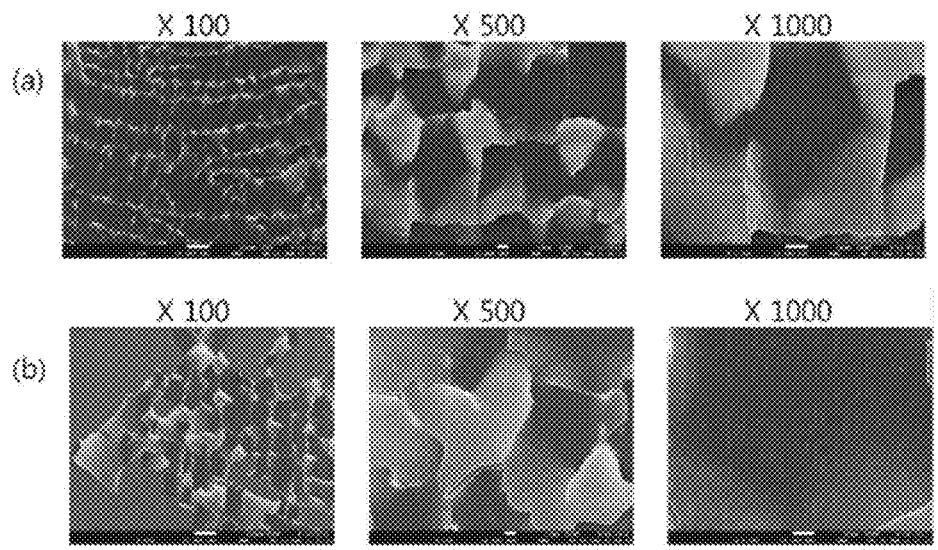
FIGS. 6(a) and 6(b) illustrate SEM images of a hydrocarbon thin film deposited for 20 minutes and 30 min, respectively.

FIG. 5 illustrates SEM images of the surface having the amorphous hydrocarbon thin film deposited for 10 minutes using acetylene gas. The uniform thin film was confirmed to be deposited via plasma polymerization on the inner surface of PTFE. Also, to check whether uniformity of the thin film layer was changed depending on the thin film deposition time and to determine the optimal thin film thickness, the deposition conditions for very uniformly depositing the thin film were examined while changing the thin film deposition time. FIGS. 6(a) and 6(b) illustrate SEM images of the amorphous hydrocarbon thin film deposited for 20 minutes and 30 min, respectively. Consequently, deposition for 10 minutes or longer led to a non-uniform surface and a cracked surface of the formed thin film. Thus, the optimal deposition time was set to 10 min. At this time, to determine the thickness of the formed hydrocarbon thin film, a silicon wafer was cut and inserted in the PTFE tube and deposition was performed under the same conditions, and the thickness of the thin film was measured using SEM. As illustrated in FIG. 7, the thickness of the thin film was measured to be 221.6 nm, and was confirmed to be 233.3 nm by alpha-step. From these two values, the thickness of the deposited thin film on the inner surface of the PTFE tube could be estimated, and the actual deposition thickness was subsequently measured using an XPS depth profile method.

Figure 8:
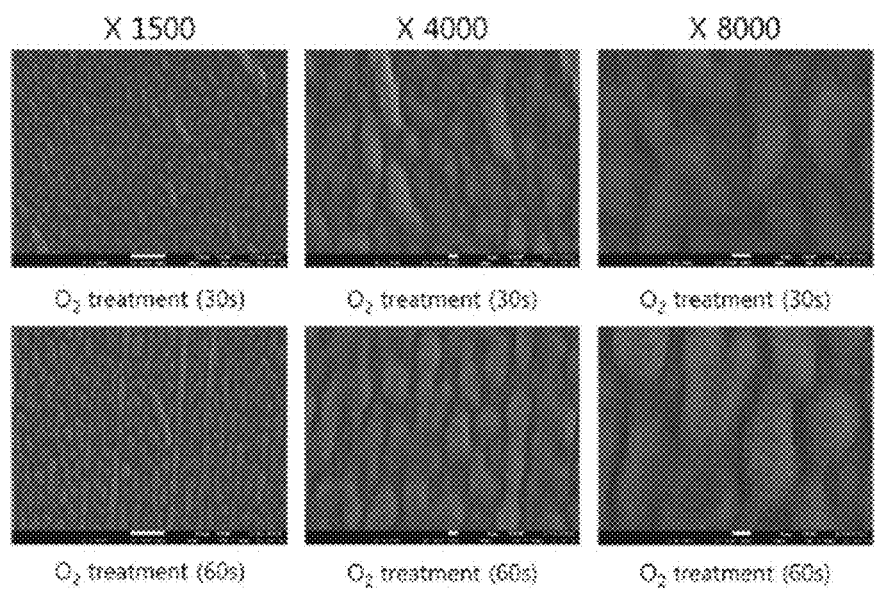
FIG. 8 illustrates SEM images depending on the oxygen plasma treatment time.

FIG. 8 illustrates SEM images of the surface modified with oxygen plasma. The surface modification process using oxygen is known possibly to progress into etching. However, upon deposition for 30~60 seconds corresponding to a comparatively short time, component coupling of the surface was changed and the effect of etching was minimized, and thereby the hydrocarbon thin film deposited in advance could be maintained.

Figure 9:
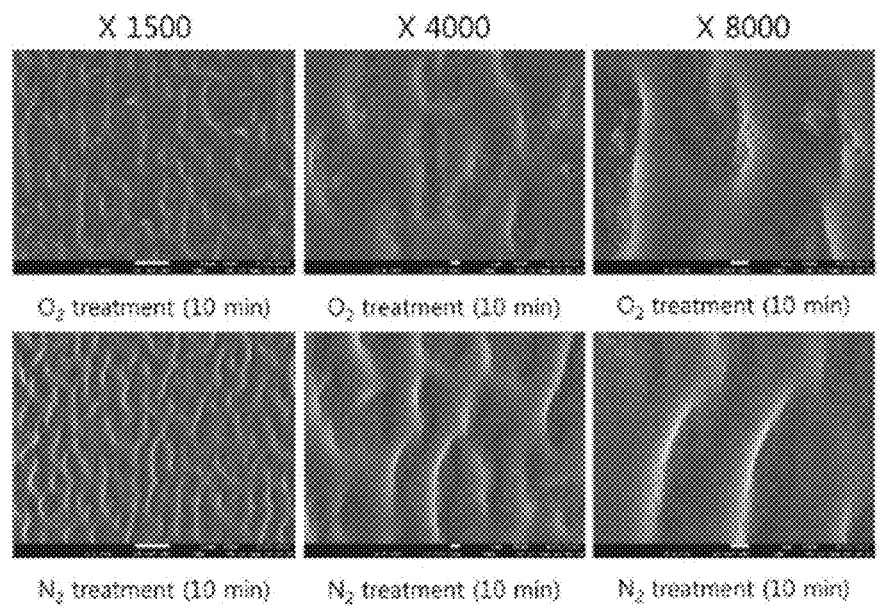
FIG. 9 illustrates SEM images of the surface modified with oxygen or nitrogen for the same time (10 min)

FIG. 9 illustrates SEM images of the inner wall of the PTFE tube subjected to surface modification, respectively, using oxygen and nitrogen plasma for the same time (10 min). Consequently, the process using nitrogen was allowed to maintain the surface of the thin film deposited in advance. In the process using oxygen, however, etching taken place due to the lengthened treatment time, and thus the thin film was partially damaged, leading to a non-uniform surface. This indicates that the surface modification process using oxygen plasma has to be completed within a short time of 10 min.

Test Example 3

Fourier Transform Infrared Spectroscopy (FT-IR)

To analyze the chemical binding state of the inner surface of a PTFE tube after modification in individual processes, FT-IR was used. The device used to measure the inner wall of the PTFE tube was Bruker vertex 70, and absorption spectrum was measured from the reflected value using attenuated total reflection. The analytical range was 4000~400 $cm^{-1}$, and a beam splitter was made of KBr. The data was analyzed using OPUS program.

Specifically, the spectrum of the PTFE tube subjected to hydrogen plasma treatment was measured, and the chemical composition thereof was thus determined. While the ratio of two gases was changed in the gas mixture of argon and hydrogen used as the reaction gas, the spectra were measured and shown together. The results are illustrated in FIG. 10. While the plasma treatment time of 10 minutes and the amount of argon gas of 10 sccm were maintained, the amount of hydrogen gas was changed from 10 to 50 sccm by intervals of 10 sccm, and thus changes in $CH_2$ component on the surface at respective concentrations were measured. If the amount of hydrogen exceeds 50 sccm, it is impossible to generate discharge. Hence, the amount of hydrogen was maximally set to 50 sccm. As is apparent from FT-IR spectrum results of FIG. 10, peaks at 1143 $cm^{-1}$ and 1200 $cm^{-1}$ corresponded to $CF_2$ stretching of PTFE, peaks at 1575 $cm^{-1}$ and 1725 $cm^{-1}$ did C=C and C=O bonds, the peak at 2850 $cm^{-1}$ did symmetric stretching of $CH_2$, and the peak at 2920 $cm^{-1}$ did asymmetric stretching of $CH_2$. In particular, through formation of $CH_2$ bonds corresponding to peaks at 2850 $cm^{-1}$ and 2920 $cm^{-1}$ and changes in the values thereof, 50 sccm was regarded as the most effective hydrogen substitution condition.

To evaluate the effects depending on the treatment time, while the ratio of argon gas and hydrogen gas was maintained at 1:5, changes in composition over time were measured. As the plasma treatment time was increased from 5 minutes to 30 minutes at intervals of 5 min, FT-IR spectra were recorded. The results are shown in FIG. 11. As shown in the results, even when the plasmas treatment time was 10 minutes or longer, additional changes in composition on the surface were not observed. Ultimately, the optimal plasma treatment time required for defluorination or hydrogenation was determined to be 10 min. Thus, the PTFE tube subjected to plasma treatment for 10 minutes using a reaction gas comprising argon and hydrogen mixed at 1:5 was employed in the subsequent additional surface modification testing.

Also, argon gas and acetylene gas at 1:2 (10 sccm:20 sccm) were fed into the hydrogen plasma treated PTFE tube to perform plasma deposition, thus depositing a hydrocarbon thin film. Then the surface was further modified by plasma treatment using oxygen (Ar:$O_2$=20 sccm:20 sccm) or nitrogen (20 sccm), and changes in chemical binding of the surface modified thin film were evaluated.

Figure 12:
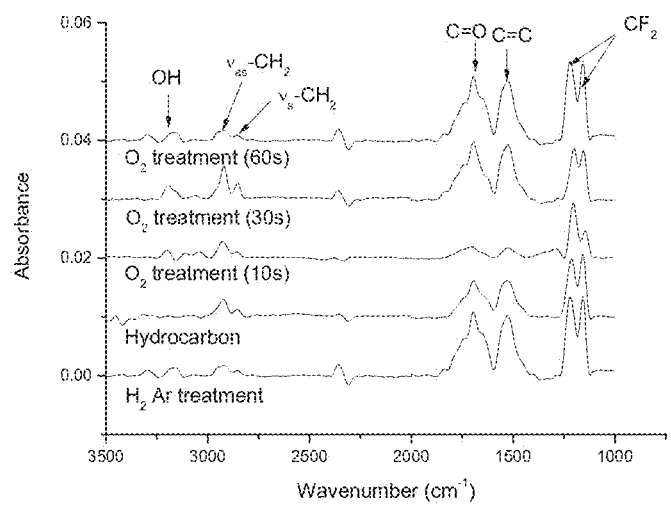
FIG. 12 illustrates FTIR-ATR spectra depending on the oxygen plasma treatment time.
Figure 13:
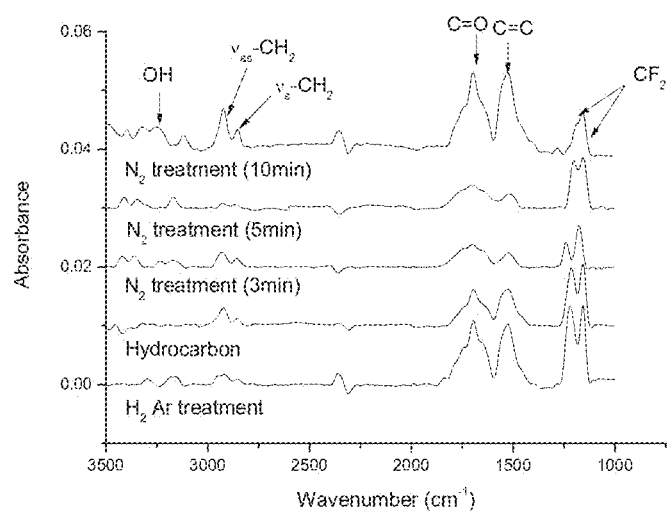
FIG. 13 illustrates FTIR-ATR spectra depending on the nitrogen plasma treatment time.

FIGS. 12 and 13 illustrate FT-IR spectra of the surface of the hydrocarbon thin film depending on the plasma treatment time using oxygen and nitrogen, respectively. Upon surface modification using oxygen plasma, peaks at 1575 $cm^{-1}$ and 1725 $cm^{-1}$ corresponding to C=C and C=O bonds were increased, whereas peaks at 2850 $cm^{-1}$ and 2920 $cm^{-1}$ corresponding to symmetric and asymmetric binding modes of $CH_2$ were decreased. This indicates that an oxygen atom was linked to the surface of the hydrocarbon thin film, instead of preexisting hydrogen. On the other hand, upon surface modification using nitrogen plasma, as the treatment time was increased, peaks at 1575 $cm^{-1}$ and 1725 $cm^{-1}$ corresponding to C=C and C=O bonds and peaks at 3300~3400 $cm^{-1}$ corresponding to C=N—H bond were increased. Furthermore, peaks at 2850 $cm^{-1}$ and 2920 $cm^{-1}$ corresponding to symmetric and asymmetric binding modes of $CH_2$ were decreased as in the treatment with oxygen plasma. This indicates that a nitrogen atom was linked to the surface of the hydrocarbon thin film, instead of preexisting hydrogen. The quantitative analysis of specific chemical components was carried out using XPS.

Test Example 4

X-Ray Photoelectron Spectroscopy (XPS)

Measurement of the binding state of the thin film is possible using FT-IR analysis of Test Example 3 but quantitative analysis is difficult using the same. Meanwhile, XPS measurement is very effective at quantitatively analyzing the chemical composition of the surface of the thin film. In the present invention, information about the composition and depth of the surface of the thin film was obtained using typical XPS and depth profile methods.

Using XPS, changes in the composition of the inner surface of the PTFE tube upon plasma treatment, formation of a nano organic thin film, and a hydrophilic surface modification process were measured. XPS was performed using PHI 5000 Versaprobe II model with monochromatic Al—K$\alpha$ (15 kV, large spot size: 800 μm, small spot size: 10 μm) as an X-ray source. To correct error generated by surface charge up, the C—H peak in the C1s spectrum was corrected to 284.5 eV. The results from the measurement were normalized based on background signals using a Shirley method, and data fitting was performed using peakfit 4.0 (Sigmaplot) and Origin 8.1 (Origin lab) software.

The amounts of the components in individual processes as analyzed by the entire XPS scan are given in Table 1 below.

TABLE 1

| Condition | % C | % F | % O | % N |
|---|---|---|---|---|
| PTFE | 32.9 ± 0.4 | 67.1 ± 0.4 | 0 | 0 |
| H$_2$ treatment | 60.5 ± 0.4 | 36.8 ± 1 | 2.8 ± 0.8 | 0 |
| Hydrocarbon | 93.3 ± 2.2 | 0 | 6 ± 1.1 | 0 |
| O$_2$ (10 s) | 78.85 ± 0.1 | 0 | 19.9 ± 1.1 | 0.3 ± 0.4 |
| O$_2$ (30 s) | 78.3 ± 0.6 | 0.85 ± 1.2 | 20.4 ± 0.0 | 0 |
| O$_2$ (60 s) | 76.5 ± 0.6 | 1 ± 1.4 | 21.3 ± 1.3 | 0 |
| N$_2$ (3 min) | 73.6 ± 0.3 | 2.2 ± 0.8 | 9.995 ± 0.6 | 14.1 ± 0.4 |
| N$_2$ (5 min) | 74 ± 1.4 | 1.8 ± 1.6 | 11.4 ± 0.2 | 14.3 ± 1.8 |
| N$_2$ (10 min) | 74.1 ± 1.2 | 0.3 ± 0.6 | 10.5 ± 1.1 | 14.6 ± 1.4 |

As is apparent from Table 1, the amount of fluorine was decreased after hydrogen plasma treatment, and when the thin film was deposited, the deposited thin film caused fluorine to disappear. The formation of oxygen or nitrogen bonds on the surface of the thin film through the surface modification process using oxygen or nitrogen was confirmed.

Figure 14:
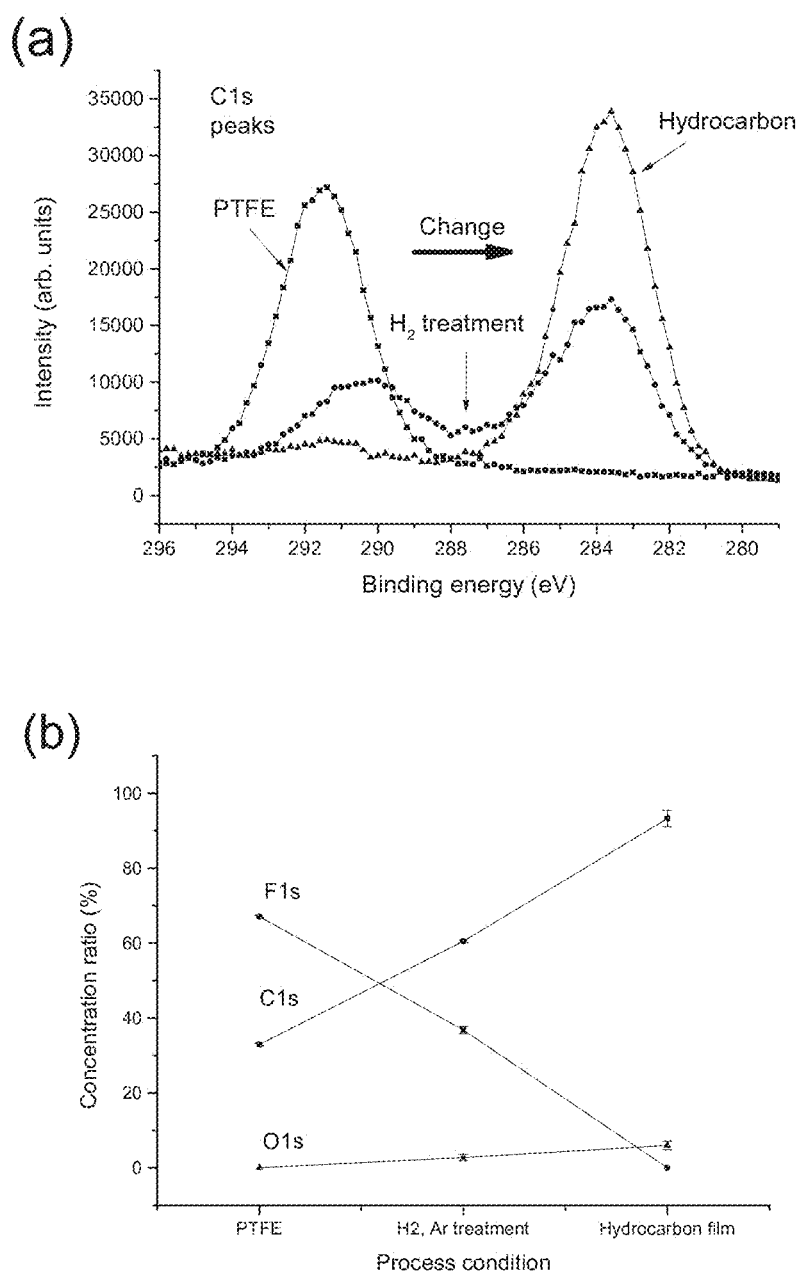
FIG. 14(a) illustrates XPS C1s spectra of the inner wall of a PTFE tube and FIG. 14(b) illustrates changes in components of the surface before and after hydrogen plasma treatment.
Figure 15:
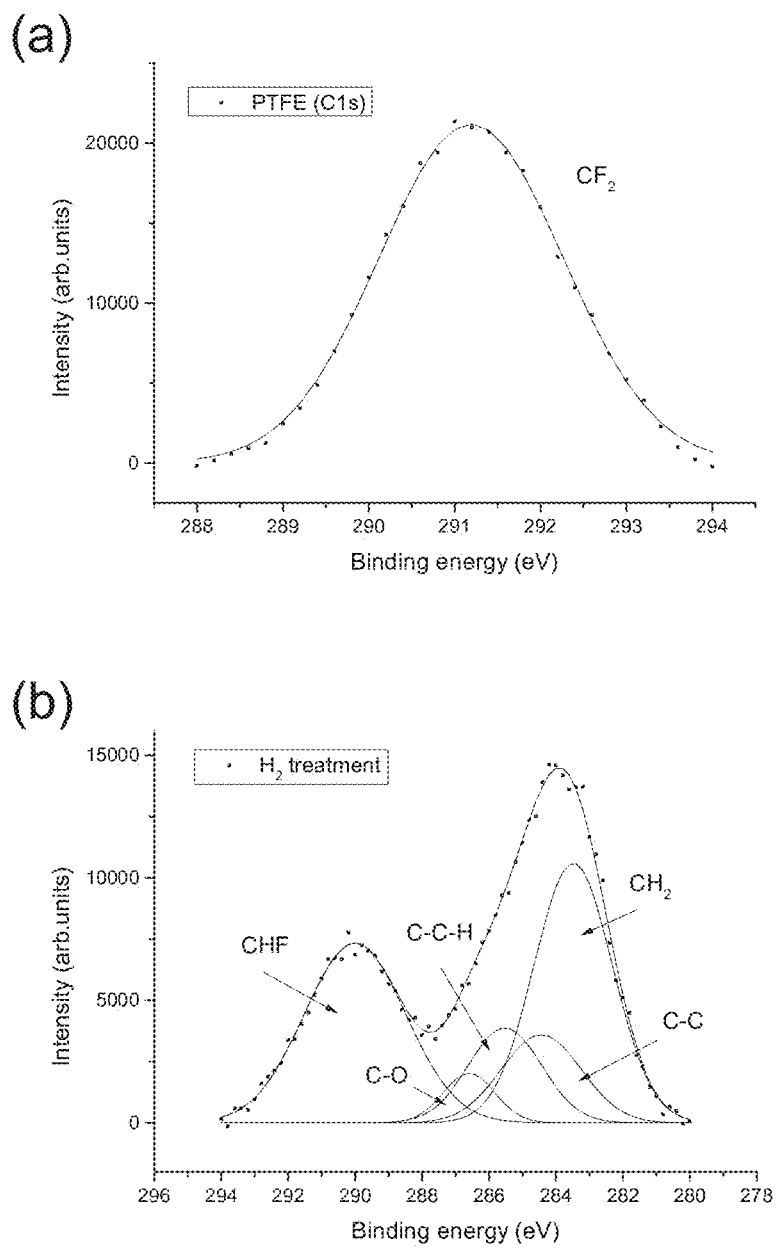
FIGS. 15(a) and 15(b) illustrate the results of analysis of XPS C1s spectra on the inner wall of a PTFE tube before and after hydrogen plasma treatment, respectively.

FIGS. 14(a) and 14(b) illustrate changes in component of the surface of PTFE before and after hydrogen plasma treatment as measured by XPS. As in FT-IR, partial defluorination of PTFE after plasma treatment occurred, and hydrogen on the surface was increased. For more detailed examination, C1s spectra were analyzed. The results are shown in FIGS. 15(a) and 15(b). The total sample analysis for CF$_2$ (291.4 eV), CH$_2$ (283.5 eV), C—C, C—H (284.5 eV), C—C—H (285.5 eV) and C—O (286.6 eV), and the component analysis for CHF (290 eV) were performed. Consequently, after hydrogen plasma treatment, the carbon component coupled with fluorine was decreased and the carbon component coupled with hydrogen was formed and increased.

Figure 16:
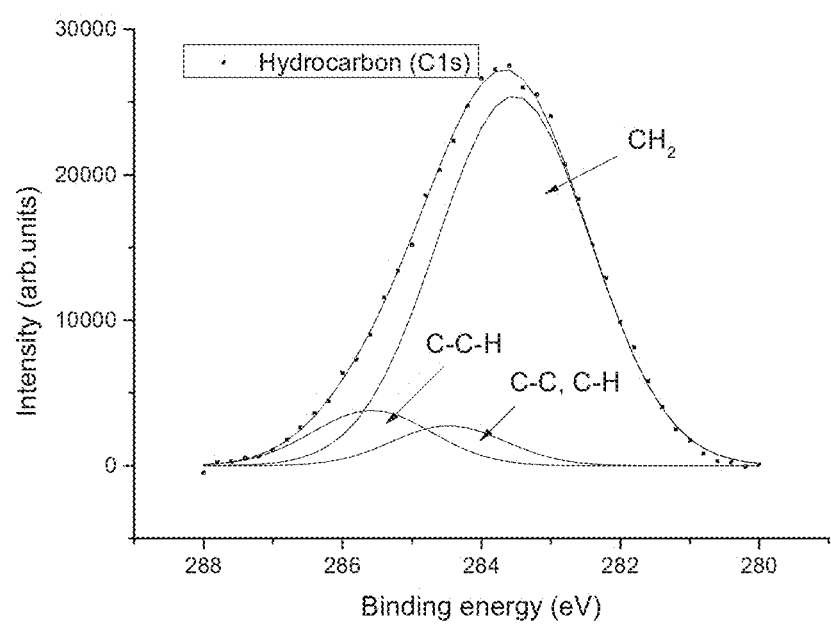
FIG. 16 illustrates C1s spectra of the hydrocarbon thin film analyzed by XPS.

After introduction of the amorphous hydrocarbon thin film via plasma polymerization using acetylene gas on the tube surface-modified with hydrogen plasma treatment, XPS analysis of the surface of the hydrocarbon thin film was performed for CH$_2$ (283.5 eV), C—C, C—H (284.5 eV), and C—C—H (285.5 eV). The results are shown in FIG. 16. As seen in this drawing, fluorine was not further detected on PTFE due to the deposition of the hydrocarbon thin film, and only the hydrocarbon component was detected. The thin film was composed mostly of CH$_2$ bonds.

Figure 17:
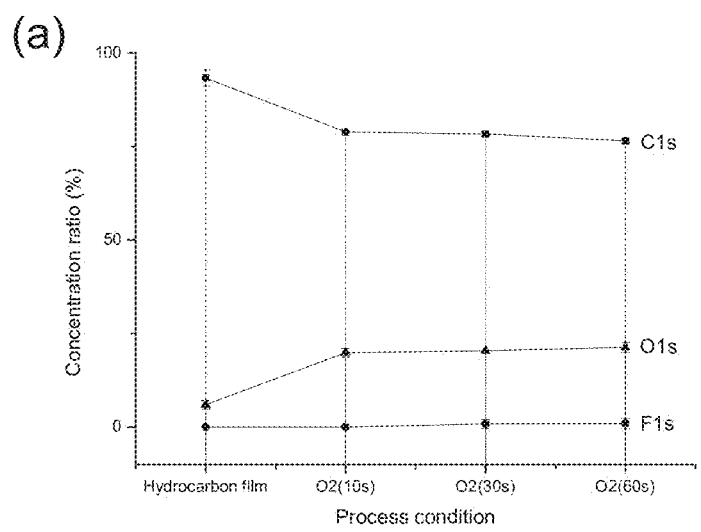
FIGS. 17(a) and 17(b) illustrate the composition ratio of the hydrocarbon thin film whose surfaces were modified by the reaction gas using oxygen and nitrogen, respectively.
Figure 17:
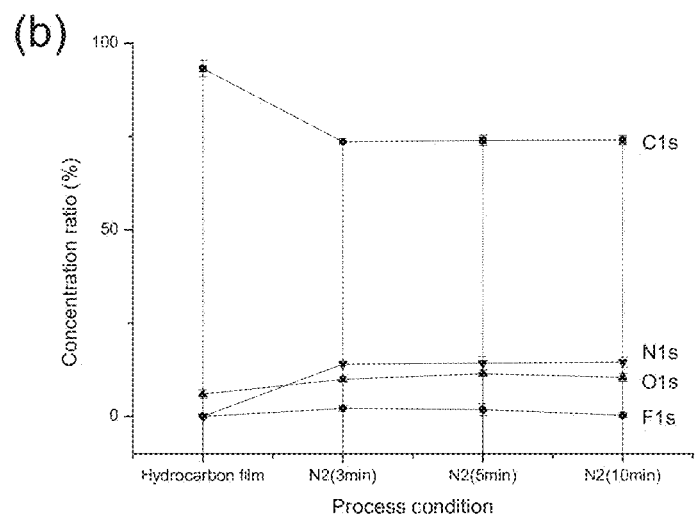
Figure 18:
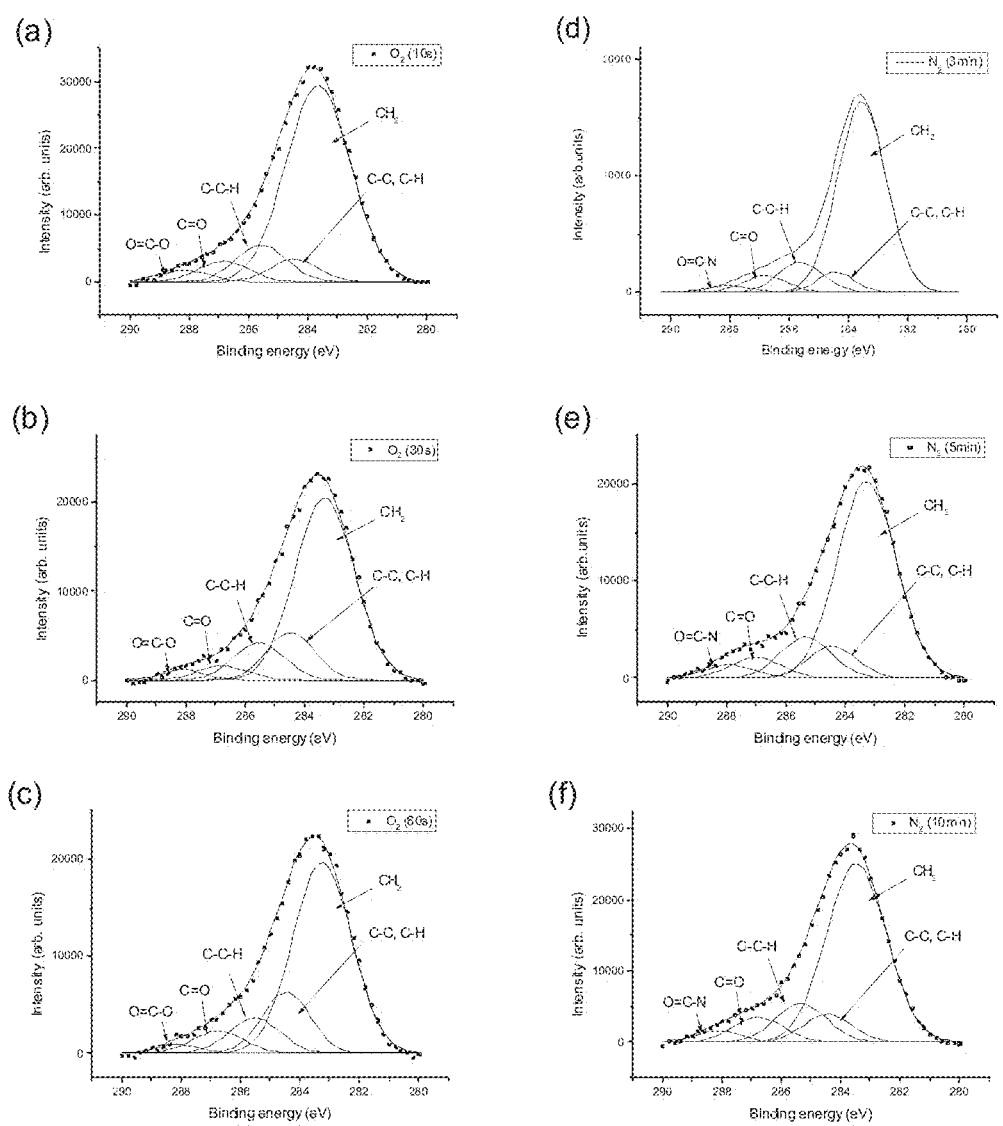
FIGS. 18(a), 18(b) and 18(c) illustrate XPS C1s spectra of the surface treated at different surface modification times of 10, 30 and 60 sec, respectively, using oxygen.
FIGS. 18(d), 18(e) and 18(f) illustrate XPS C1s spectra of the surface treated at different surface modification times of 3, 5 and 10 min, respectively, using nitrogen.

The surface of hydrocarbon introduced via plasma polymerization of acetylene gas was modified using oxygen or nitrogen plasma, and then changes in the surface thereof were analyzed by XPS. The composition ratios of the resulting surface-modified hydrocarbon thin film are illustrated in FIGS. 17(a) and 17(b). FIG. 17(a) illustrates the composition of the sample after oxygen plasma treatment and FIG. 17(b) illustrates the composition of the sample after nitrogen plasma treatment. As seen in these drawings, the proportion of C1s was decreased and oxygen or nitrogen was linked to the surface of the thin film.

To ascertain the difference in the composition depending on modification process time by the reaction gas, oxygen and nitrogen, C1s spectra were recorded. The results are shown in FIGS. 18A to 18F. Upon surface modification using oxygen, component analysis was performed for CH$_2$ (283.5 eV), C—C, C—H (284.5 eV), C—C—H (285.5 eV), C=O (286.8 eV) and O—C=O (288.1 eV), and upon surface modification using nitrogen, component analysis was conducted for CH$_2$ (283.5 eV), C—C, C—H (284.5 eV), C—C—H (285.5 eV), C=O (286.8 eV) and O=C—N (288.1 eV). In accordance with the progress of the surface modification of the thin film using oxygen, the C—C component was increased and the oxygen bond was formed. In particular, an increase in the C—C component indicates that the hydrocarbon thin film was partially etched by oxygen plasma.

The composition ratios of C1s spectra depending on the surface modification process time using oxygen and nitrogen are given in Tables 2 and 3 below, respectively.

TABLE 2

| | Chemical composition in at (%) | | | | |
|---|---|---|---|---|---|
| Process condition | CH$_2$ | C—C, C—H | C—C—H | C=O | O—C=O |
| Hydrocarbon | 84.2 | 7.1 | 8.7 | 0 | 0 |
| O$_2$ 10 s | 66.9 | 9.4 | 15.1 | 4.9 | 3.7 |
| O$_2$ 30 s | 63.9 | 20.1 | 9.8 | 3.7 | 2.5 |
| O$_2$ 60 s | 58.6 | 21.7 | 13 | 5.2 | 1.5 |

TABLE 3

| | Chemical composition in at (%) | | | | |
|---|---|---|---|---|---|
| Process condition | CH$_2$ | C—C, C—H | C—C—H | C=O | N—C=O |
| Hydrocarbon | 84.2 | 7.1 | 8.7 | 0 | 0 |
| N$_2$ 3 min | 75.2 | 5.8 | 10.7 | 6.7 | 1.6 |
| N$_2$ 5 min | 68.6 | 11.6 | 10.6 | 5 | 4.2 |
| N$_2$ 10 min | 64.2 | 10.4 | 17.1 | 4.8 | 3.5 |

In the case of oxygen surface modification, the surface of the thin film was confirmed to be hydrophilic via an increase in C=O component. Also, an increase in C—C and C—H components indicates that the thin film composed of CH$_2$ was etched by oxygen plasma in hydrocarbon matrix. The formation of nitrogen bond was confirmed via surface modification of the thin film using nitrogen. The reason why changes in C—C and C—H components were small is that nitrogen surface modification changes only the chemical binding of the surface of the thin film and generates no etching. In the case of nitrogen surface modification, the nitrogen-carbon bond is present but the portion of hydrophobic hydrocarbon is maintained higher and thus hydrophilicity is considered to be lower, compared to when using oxygen treatment.

Figure 19:
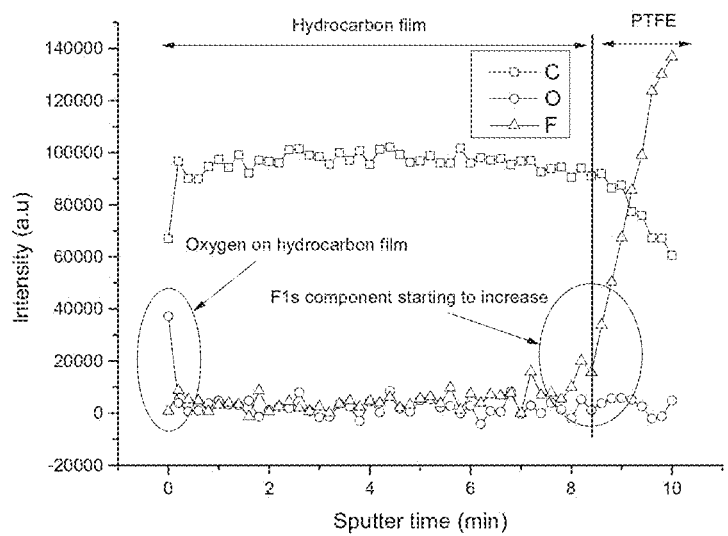
FIG. 19 illustrates changes in component of the surface modified via oxygen treatment for 30 seconds as measured by XPS at different depths.

To analyze the chemical composition depending on the depth of the thin film surface-modified with oxygen, an XPS depth profile method was used. The surface of the thin film was sputtered for 10 minutes (50 cycles) using an Ar ion gun (3 kV), and thus the composition distribution at different depths was analyzed. At 3 kV, sputtering of the thin film was conducted by about 30 nm each per 1 cycle. Changes in individual components depending on the sputtering time were measured. The results are shown in FIG. 19. This measurement was implemented on the sample subjected to surface modification with oxygen for 30 sec.

As is apparent from the results of the composition ratio depending on the depth measured by XPS depth profile, the oxygen component was decreased after only 1 cycle, from which it can be ascertained that oxygen was linked to the depth of 30 nm from the surface and the oxygen component linked to the surface of the thin film exhibited hydrophilicity. Also, the fluorine component started being detected after about 8 minutes (40 cycles). Because the thin film is sputtered by 30 nm per 1 cycle as mentioned above, in the case of 40 cycles, the corresponding depth approximates to 240 nm. Thereby, the thickness of the amorphous hydrocarbon thin film actually deposited on the inner surface of the PTFE tube was determined to be about 240 nm, which is similar to the thickness of the amorphous hydrocarbon thin film deposited on the silicon wafer as measured by SEM and alpha-step.

Figure 20:
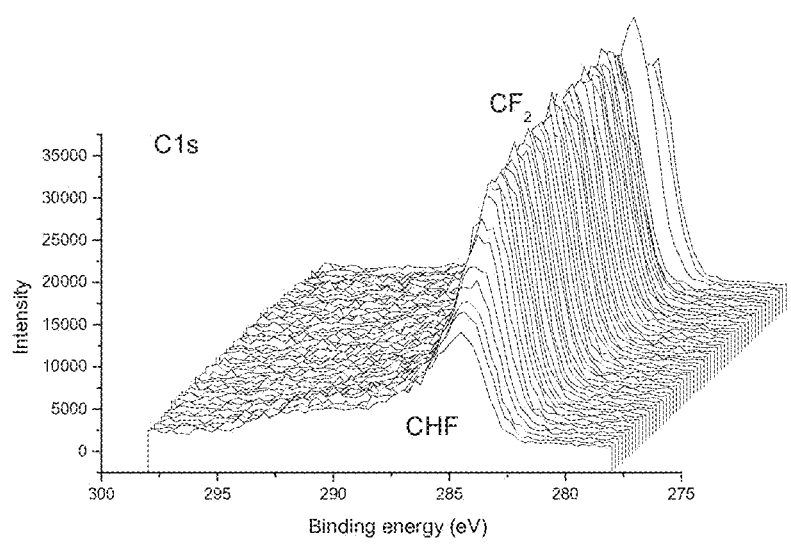
FIG. 20 illustrates XPS C1s spectra of the surface modified via oxygen treatment for 30 seconds at different depths.

A waterfall graph for the C1s spectra of XPS depth profile is shown in FIG. 20. After 10 minutes (50 cycles) using an Ar ion gun at 3 kV, $CH_2$ which is present in the greatest amount among the components of the amorphous hydrocarbon thin film in the C1s spectra was gradually decreased as sputtering progressed, and CHF in which fluorine was partially substituted by hydrogen was gradually increased. The portion where CHF was detected designates the surface of the PTFE tube substituted with hydrogen via hydrogen plasma treatment.

Test Example 5

Measurement of Water Contact Angle (WCA)

Figure 22:
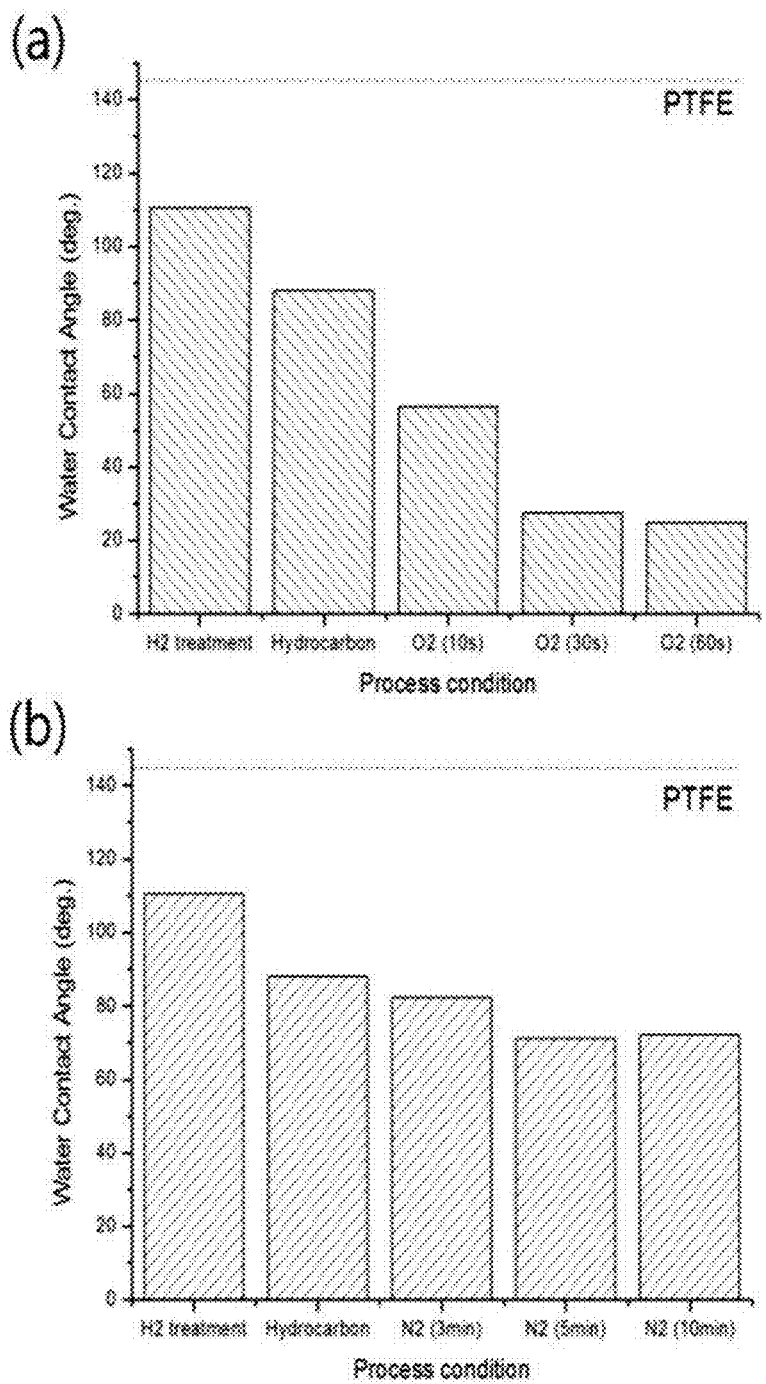
FIGS. 22(a) and 22(b) illustrate changes in water contact angle depending on preparation conditions in tubes whose surfaces were modified with oxygen and nitrogen, respectively.

As for changes in surface energy of the surface of the tube manufactured as above, hydrophilicty/hydrophobicity was determined by measuring a water contact angle. A tube was cut into pieces, and water contact angles on curved surfaces of the pieces of the tube were measured. Because the uneven inner surface of a piece of the tube having a small inner diameter is tested, it is difficult to accurately measure the angle, but surface energy is determined via changes in relative values. Using a sessile drop method on a piece of the tube, 3 µl of deionzied water was dropped onto the surface of a substrate, and the contact angle of the water drop was measured using a CCD camera. The obtained image and the water contact angle determined therefrom are illustrated FIGS. 21 and 22, respectively.

The results of changes in water contact angle for oxygen surface modification may be associated with the composition ratio of XPS. As seen in the composition ratio of XPS, as the oxygen surface modification time increased, the proportion of oxygen was increased and the water contact angle was decreased. This means that the surface of the thin film becomes hydrophilic in the presence of more oxygen bonds. Also, in the case of nitrogen surface modification, about 10% oxygen was contained, but even when the proportion of nitrogen was higher, it did not have a great influence on hydrophilic effects. Accordingly, the water contact angle was confirmed to vary depending on the proportion of oxygen contained in the surface of the thin film.

Test Example 6

Optical Microscopy and Cell Staining

In order to investigate attachment of rat vascular smooth muscle cells on tube specimens cut lengthwise, the end sides of the specimens were well enveloped to prevent outflushing of the culture medium. A cell culture on the inner surface of the tube modified to be hydrophilic was observed using an optical microscope and observed with the naked eye via cytoplasmic staining. The cells cultured on the surface of the tube were observed using an optical microscope (GX41, magnification ×10, Olympus), thus evaluating whether smooth muscle cells were adhered to the inner surface of the tube. Also, to easily observe attachment of the cells with the naked eye, cytoplasms were stained with eosin B (Sigma Aldrich).

The cells were aliquoted into the tube resulting from individual surface modification processes, and then cultured for 24 hr in an incubator. To observe the extent of actual adhesion of the cells with the naked eye, cytoplasms were stained with eosin B, after which changes in color of the inner wall of the PTFE tube were observed and taken by a camera. The results are shown in FIG. 23. As seen in these images, the red portion in the tube shows cell attachment. In particular, in the tube treated with oxygen, deep red (especially, 30 seconds and 60 sec) was shown, and the tube treated with nitrogen manifested slight red (5 minutes and 10 min). Accordingly in order to improve adhesion of smooth muscle cells, it was preferable that oxygen content and hydrophilicity be increased on the inner wall of the PTFE tube.

To observe whether the cells were actually adhered to the inner wall of the tube stained with red, the morphology of the adhered cells was observed using an optical microscope. The results are shown in FIG. 24, which illustrates optical microscope images of the tubes treated with oxygen or nitrogen having the red stained inner walls through cytoplasmic staining using eosin B. As seen in FIG. 24, a plurality of smooth muscle cells was adhered to the inner wall of the tube treated with oxygen, and the smooth muscle cells were partially attached to the tube treated with nitrogen as well. As is apparent from the microscope images, adhesion of the smooth muscle cells on the tube treated with oxygen plasma for 60 seconds was evaluated to be the greatest. This is considered to be because the tube inner surface of which is modified to be hydrophilic according to the present invention is improved in adhesion of smooth muscle cells, and thus enables adherent culture of endothelial cells of the vessel wall, making it possible to mimic artificial blood vessels. Therefore, the tube of the invention has active applications in a variety of fields.

As described hereinbefore, the present invention provides a tube with a modified inner wall surface using plasma and a preparation method for the same. According to the present invention, the inner surface of an inert tube is modified using microplasma by sequentially performing 1) modifying the surface to have reactivity, 2) introducing a hydrocarbon thin film layer, and 3) additionally modifying the surface to enhance cell adhesion, so that the inner surface of the tube thus modified can be enhanced in adhesion of smooth muscle cells thereon, and thus such a tube can be utilized as artificial blood vessels transplantable in vivo, etc. In particular, using the preparation method by microplasma treatment enables the inner surface of a tube having an inner diameter as small as a few of mm to be uniformly modified.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A preparation method of a tube having an inner diameter of 4 mm or less, comprising modifying an entire inner surface of the tube by:
   placing an electrode over a part of the tube and creating a vacuum condition inside the tube; and
   adding a reaction gas into the tube under the vacuum condition and generating plasma to treat the entire inner surface of the tube including an inner portion corresponding to the part of the tube placed with the electrode,
   wherein an inner wall of the tube is enhanced in cell adhesion.

2. The preparation method of claim 1, wherein the modifying of the inner surface using plasma adjusts an extent of hydrophilicity and hydrophobicity of the inner surface of the tube by changing reaction conditions.

3. The preparation method of claim 1, wherein the tube is a superhydrophobic fluorinated hydrocarbon polymer tube made of a material selected from the group consisting of polytetrafluoroethylene (PTFE), a fluorinated ethylene propylene copolymer (FEP), an ethylene tetrafluoroethylene copolymer, ethylene chlorotrifluoroethylene (ETFE), perfluoroalkoxy (PFA) and polyvinyliden fluoride (PVDF); a biocompatible polymer tube made of a material selected from the group consisting of polyethylene terephthalate (PET), poly(2-hydroxyethyl methacrylate) (PHEMA), polyvinylpyrrolidone (PVP), polyethylene (PE), polyethylene glycol (PEG a.k.a. polyethylene oxide; PEO or polyoxyethylene; POE), polyvinyl alcohol (PVOH, PVA or PVAI), polypropylene (PP) and polyurethane (PU); or a metal tube made of a material selected from the group consisting of nitinol (NiTi), titanium, stainless steel 316L (SUS 316L) and a cobalt-chromium alloy.

4. The preparation method of claim 1, further comprising modifying a surface of a surface modification layer of the tube using microplasma so as to have reactivity.

5. The preparation method of claim 4, further comprising modifying a surface of a thin film layer formed on the surface modification layer so as to enhance cell adhesion of the inner surface of the tube.

6. The preparation method of claim 4, wherein the modifying of the surface of the surface modification layer is performed using, as the reaction gas, a gas mixture of oxygen and argon or a gas mixture of nitrogen and argon.

7. The preparation method of claim 6, wherein the modifying of the surface of the surface modification layer is performed for 20~80 seconds when using oxygen as the reaction gas, or is performed for 4~8 minutes when using nitrogen as the reaction gas.

8. The preparation method of claim 4, wherein the microplasma is formed by atmospheric pressure discharge.

9. A preparation method of a tube having an inner diameter of 4 mm or less, comprising modifying an entire inner surface of the tube by:
   placing an electrode over a part of the tube and creating a vacuum condition inside the tube; and
   adding a reaction gas into the tube under the vacuum condition and generating plasma to treat the entire inner surface of the tube including an inner portion corresponding to the part of the tube placed with the electrode; and
   forming a thin film layer that enhances cell adhesion of the inner surface of the tube.

10. The preparation method of claim 9, wherein the modifying is performed using a gas mixture of hydrogen and argon as the reaction gas.

11. The preparation method of claim 10, wherein the gas mixture comprises argon gas and hydrogen gas at a volume ratio of 1:3~1:7.

12. The preparation method of claim 10, wherein the modifying comprises substituting a fluorine-carbon bond of a fluorinated hydrocarbon polymer with a hydrogen-carbon bond.

13. A preparation method of a tube having an inner diameter of 4 mm or less, comprising modifying an entire inner surface of the tube by:
   placing an electrode over a part of the tube and creating a vacuum condition inside the tube;
   adding a reaction gas into the tube under the vacuum condition and generating plasma to treat the entire inner surface of the tube including an inner portion corresponding to the part of the tube placed with the electrode; and
   forming a hydrocarbon thin film layer on a surface modification layer that prevents aging or imparts adhesiveness to the inner surface of the tube,
   wherein the forming of the thin film layer is performed by accumulating a hydrocarbon precursor using plasma to form a plasma-polymerized thin film layer.

14. The preparation method of claim 13, wherein the hydrocarbon film layer is formed via plasma polymerization using a gas mixture of acetylene and argon.

15. The preparation method of claim 14, wherein the hydrocarbon film layer has a thickness of 50~250 nm.

16. A preparation method of a tube, comprising:
   preparing a tube;
   modifying an inner surface of the tube using microplasma so as to have reactivity;
   forming a thin film layer on the modified surface of the tube to prevent aging or impart adhesiveness; and
   modifying a surface of the thin film layer using microplasma so as to enhance cell adhesion thereon.

* * * * *